US007973114B2

(12) United States Patent
Mihan et al.

(10) Patent No.: US 7,973,114 B2

(45) Date of Patent: Jul. 5, 2011

(54) MONOCYCLOPENTADIENYL COMPLEXES

(75) Inventors: Shahram Mihan, Bad Soden (DE); Ilya Nifant'ev, Moscow (DE)

(73) Assignee: Basell Polyolefine GmbH, Wesseling (DE)

(*) Notice: Subject to any disclaimer, the term of this patent is extended or adjusted under 35 U.S.C. 154(b) by 741 days.

(21) Appl. No.: 11/981,473

(22) Filed: Oct. 31, 2007

(65) Prior Publication Data

US 2008/0064838 A1 Mar. 13, 2008

Related U.S. Application Data

(63) Continuation of application No. 10/539,342, filed as application No. PCT/EP03/14447 on Dec. 18, 2003, now Pat. No. 7,541,473.

(60) Provisional application No. 60/490,303, filed on Jul. 25, 2003.

(30) Foreign Application Priority Data

Dec. 20, 2002 (DE) ................................. 102 61 109

(51) Int. Cl.

*C08F 4/69* (2006.01)
*C08F 4/52* (2006.01)
*B01J 31/00* (2006.01)
*C07F 11/00* (2006.01)

(52) U.S. Cl. ........ 526/161; 526/172; 526/160; 526/170; 526/169; 502/103; 502/117; 556/52; 556/42; 556/58

(58) Field of Classification Search .................... 556/58, 556/52, 43; 526/172, 161, 169
See application file for complete search history.

(56) References Cited

U.S. PATENT DOCUMENTS

| | | | | |
|---|---|---|---|---|
| 3,125,547 | A | 3/1964 | Blatz | |
| 3,242,150 | A | 3/1966 | Scoggin | |
| 3,248,179 | A | 4/1966 | Norwood | |
| 3,709,853 | A | 1/1973 | Karapinka | |
| 4,015,059 | A | 3/1977 | Karol | |
| 5,227,440 | A | 7/1993 | Canich et al. | |
| 5,246,783 | A | 9/1993 | Spenadel et al. | |
| 5,281,679 | A | 1/1994 | Jejelowo et al. | |
| 5,698,642 | A | 12/1997 | Govoni et al. | |
| 6,255,418 | B1 | 7/2001 | Jolly et al. | |
| 6,281,153 | B1 | 8/2001 | Becke et al. | |
| 6,326,445 | B1 | 12/2001 | Wenzel | |
| 6,350,814 | B1 | 2/2002 | Bauer et al. | |
| 6,413,477 | B1 | 7/2002 | Govoni et al. | |
| 6,417,302 | B1 | 7/2002 | Bohnen | |
| 6,420,507 | B1 | 7/2002 | Kale et al. | |
| 6,437,161 | B1 * | 8/2002 | Mihan et al. | 556/11 |
| 6,444,606 | B1 | 9/2002 | Bingel et al. | |
| 6,492,539 | B1 | 12/2002 | Bingel et al. | |
| 6,589,905 | B1 | 7/2003 | Fischer et al. | |
| 6,620,953 | B1 | 9/2003 | Bingel et al. | |
| 6,642,313 | B1 | 11/2003 | Kazakov et al. | |
| 6,699,948 | B2 | 3/2004 | Mihan et al. | |
| 6,723,675 | B1 | 4/2004 | Wang | |
| 6,737,130 | B2 | 5/2004 | Ferri | |
| 6,784,261 | B1 | 8/2004 | Schopf et al. | |
| 6,787,498 | B2 | 9/2004 | Mihan et al. | |
| 6,812,185 | B2 | 11/2004 | Fischer et al. | |
| 6,838,563 | B2 | 1/2005 | Mihan et al. | |
| 6,900,343 | B1 | 5/2005 | Bingel et al. | |
| 6,911,516 | B1 | 6/2005 | Mihan et al. | |
| 6,919,412 | B1 | 7/2005 | Mihan et al. | |
| 6,924,248 | B2 | 8/2005 | Mihan et al. | |
| 6,963,017 | B2 | 11/2005 | Bingel et al. | |
| 7,038,070 | B2 | 5/2006 | Bingel et al. | |
| 7,045,644 | B2 | 5/2006 | Schopf et al. | |
| 7,053,160 | B1 | 5/2006 | Bingel et al. | |
| 7,094,724 | B2 | 8/2006 | Fraaije et al. | |
| 7,238,818 | B2 | 7/2007 | Ewen et al. | |
| 7,507,688 | B2 | 3/2009 | Mihan et al. | |
| 7,534,847 | B2 * | 5/2009 | Mihan et al. | 526/348 |
| 7,619,090 | B2 * | 11/2009 | Mihan et al. | 546/153 |
| 2003/0036658 | A1 | 2/2003 | Mihan et al. | |
| 2003/0036662 | A1 | 2/2003 | Mihan et al. | |
| 2003/0055267 | A1 | 3/2003 | Mihan et al. | |
| 2003/0176275 | A1 | 9/2003 | Fraaije et al. | |
| 2003/0236164 | A1 | 12/2003 | Fischer et al. | |
| 2004/0033890 | A1 | 2/2004 | Mihan et al. | |
| 2004/0242880 | A1 | 12/2004 | Mihan et al. | |

FOREIGN PATENT DOCUMENTS

| | | |
|---|---|---|
| DE | 19630580 | 2/1998 |
| DE | 19710615 | 9/1998 |
| DE | 19745047 | 4/1999 |
| EP | 100843 | 2/1984 |
| EP | 416815 | 3/1991 |
| EP | 420436 | 4/1991 |
| EP | 608369 | 8/1994 |
| EP | 662989 | 7/1995 |
| EP | 728160 | 8/1996 |

(Continued)

OTHER PUBLICATIONS

S. Arndt, "Alkyl Complexes of Rare-Earth Metals That Contain a Furyl-Functionalized Cyclopentadienyl Ligand: Alkyl Cation Formation and Unexpected Ring-Opening Reaction of the Furyl Group," *Organometallics*, vol. 22, p. 775-781 (2003).

S. Pang et al., "Size-Exclusion Chromatographic Assessment of Long-Chain Branch Frequency in Polyethylenes," *Chromatography of Polymers*, ACS Symposium Series 521, edited by Theodore Provder, p. 254-269 (1993).

L. Wild, "Temperature Rising Elution Fractionation," *Advances in Polymer Science 98*, p. 1-47 (1999).

B. Monrabal, "Crystallization Analysis Fractionation: A New Technique for the Analysis of Branching Distribution in Polyolefins," *J. of Applied Polymer Science*, vol. 52, p. 491-499 (1994).

(Continued)

*Primary Examiner* — Rip A. Lee

(57) ABSTRACT

Monocyclopentadienyl complexes in which the cyclopentadienyl system bears at least one unsubstituted, substituted or fused, heteroaromatic ring system bound via a specific bridge, a catalyst system comprising at least one of the monocyclopentadienyl complexes, the use of the catalyst system for the polymerization or copolymerization of olefins and a process for preparing polyolefins by polymerization or copolymerization of olefins in the presence of the catalyst system and polymers obtainable in this way.

3 Claims, No Drawings

FOREIGN PATENT DOCUMENTS

| | | | |
|---|---|---|---|
| EP | 742046 | | 11/1996 |
| EP | 899278 | | 3/1999 |
| WO | 90/03414 | | 4/1990 |
| WO | 91/09882 | | 7/1991 |
| WO | 93/03093 | | 2/1993 |
| WO | 93/12151 | | 6/1993 |
| WO | 95/27005 | | 10/1995 |
| WO | 96/00243 | | 1/1996 |
| WO | 96/13529 | | 5/1996 |
| WO | 97/04015 | | 2/1997 |
| WO | 97/36937 | | 10/1997 |
| WO | 98/03559 | | 1/1998 |
| WO | 98/22486 | | 5/1998 |
| WO | 98/27124 | | 6/1998 |
| WO | 98/40419 | | 9/1998 |
| WO | 98/44011 | | 10/1998 |
| WO | 99/06414 | | 2/1999 |
| WO | 00/05277 | | 2/2000 |
| WO | 00/24787 | | 5/2000 |
| WO | 00/31090 | | 6/2000 |
| WO | 01/09148 | | 2/2001 |
| WO | 01/12641 | | 2/2001 |
| WO | 01/12687 | | 2/2001 |
| WO | WO 01/12641 | A1 * | 2/2001 |
| WO | 01/41920 | | 6/2001 |
| WO | 01/92346 | | 12/2001 |
| WO | 01/96417 | | 12/2001 |
| WO | 03/024982 | | 3/2003 |
| WO | WO 03/024982 | A1 * | 3/2003 |
| WO | 2004/056481 | | 7/2004 |
| WO | 2004/056878 | | 7/2004 |

OTHER PUBLICATIONS

M. Enders et al., "New Chromium (III) Complexes as Highly Active Catalysts for Olefin Polymerization," *Organometallics*, vol. 20(24), p. 5005-5007 (2001) XP-001112032.

S. Bradley et al., "Synthesis and Structure of Amino-Functionalized Cyclopentadienyl Vanadium Complexes and Evaluation of Their Butadiene Polymerization Behavior," *Organometallics*, vol. 21(16), p. 3443-3453 (2002).

G. Kraus et al., "A Method for Characterization of Long-Chain Branched Polymers by GPC and Intrinsic Viscosity," *J. Polymer Sci.: Symposium* No. 43, p. 329-343 (1973).

M. Pollard et al., "Observation of Chain Branching in Polyethylene in the Solid State and Melt via $^{13}C$ NMR Spectroscopy and Melt NMR Relaxation Time Measurements," *Macromolecules*, vol. 37(3), p. 813,825 (2004).

R. Koopmans, "Extrudate Swell of High Density Polyethylene. Part I: Aspects of Molecular Structure and Rheological Characterization Methods," *Polymer Engineering and Science*, vol. 32(23), p. 1741-1749 (1992).

J. Vega et al., "Small-Amplitude Oscillatory Shear Flow Measurements as a Tool To Detect Very Low Amounts of Long Chain Branching in Polyethylenes," *Macromolecules*, vol. 31(11), p. 3639-3647 (1998).

P. Wood-Adams et al., "Effect of Molecular Structure on the Linear Viscoelastic Behavior of Polyethylene," *Macromolecules*, vol. 33(20), p. 7489-7499 (2000).

C. Piel et al., "Structure-Property Relationships of Linear and Long-Chain Branched Metallocene High-Density Polyethylenes Characterized by Shear Rheology and SEC-MALLS," *Macromolecular Chemistry and Physics*, vol. 207, p. 26-38 (2006).

W. Kaminsky et al., "Polymerization of Ethene and Longer Chained Olefins by Metallocene Catalysis," *Macromol. Symp.*, vol. 226, p. 25-34 (2005).

K. Klimke et al., "Optimisation and Application of Polyolefin Branch Quantification by Melt-State $^{13}C$ NMR Spectroscopy," *Macromol. Chem. Phys.*, vol. 207, p. 382-395 (2006).

S. Bin Wadud et al., "Shear and extensional rheology of sparsely branched metallocene-catalyzed polyethylenes," *J. Rheol.*, vol. 44(5), p. 1151-1167 (2000).

D. Yan et al., "Effect of long chain branching on rheological properties of metallocene polyethylene," *Polymer*, vol. 40, p. 1737-1744 (1999).

F. Stadler et al., "Influence of type and content of very long comonomers on long-chain branching of ethene-/α-olefin copolymers," *Macromolecules*, vol. 39(4), p. 1474-1500 (2006).

J. Janzen et al., "Diagnosing long-chain branching in polyethylenes," *Journal of Molecular Structure*, vol. 485-486, p. 569-584 (1999).

C. Gabriel et al., "Analytical and rheological characterization of long-chain branched metallocene-catalyzed ethylene homopolymers," *Polymer*, vol. 43, p. 6383-6390 (2002).

B. Zimm et al., "Dimension of Chain Molecules Containing Branches and Rings," *The Journal of Chemical Physics*, vol. 17(12), p. 1301-1314 (1949).

H. Barth et al., *Modern Methods of Polymer Characterization*, Chemical Analysis, vol. 113, New York: Wiley (1991); Table of Contents.

Hadjichristidis et al., "Well-Defined, Model Long Chain Branched Polyethylene. 1. Synthesis and Characterization," *Macromolecules*, vol. 33(7), p. 2424-2436 (2000).

E. Kokko et al., "Long-Chain Branched Polyethylene via Metallocene-Catalysis: Comparison of Catalysts," Contribution in *Organometallic Catalysts and Olefin Polymerization* by R. Blom et al., p. 335-345 (2001).

J. Stange et al., "Rheological behavior of blends from a linear and a long-chain branched polypropylene," *J. Rheol.*, vol. 49(5), p. 1059-1079 (2005).

H. Münstedt et al., "Rheological measuring techniques and their relevance for the molecular characterization of polymers," *J. Non-Newtonian Fluid Mech.*, vol. 128, p. 1-8 (2005).

T. McLeish et al., "Molecular constitutive equations for a class of branched polymer: The pom-pom polymer," *J. Rheol.*, vol. 42(1), p. 81-110 (1998).

I. Vittorias et al., "Detection and quantification of industrial polyethylene branching topologies via Fourier-transform rheology, NMR and simulation using the Pom-pom model," *Rheol. Acta*, vol. 46, p. 321-340 (2007).

E. van Ruymbeke et al., "A sensitive method to detect very low levels of long chain branching from the molar mass distribution and linear viscoelastic response," *J. Rheol.*, vol. 49(6), p. 1-18 (2005).

S. Trinkle et al., "Van Gurp—Palmen Plot II—classification of long chain branched polymers by their topology," *Rheol Acta*; vol. 41, p. 103-113 (2002).

D. Lohse et al., "Well-Defined, Model Long Chain Branched Polyethylene. 2. Melt Rheological Behavior," *Macromolecules*, vol. 35(8), p. 3066-3075 (2002).

C. Gabriel et al., "Influence of long-chain branches in polyethylenes on linear viscoelastic flow properties in shear," *Rheol Acta*, vol. 41, p. 232-244 (2002).

B. Bersted et al., "Prediction of Rheological Behavior of Branched Polyethylene from Molecular Structure," *Journal of Applied Polymer Science*, vol. 26, p. 1001-1014 (1981).

B. Bersted, "On the Effects of Very Low Levels of Long Chain Branching on Rheological Behavior in Polyethylene," *J. of Applied Polymer Science*, vol. 30, p. 3751-3765 (1985).

H. Park et al., "Influence of long-chain branching on time-pressure and time-temperature shift factors for polystyrene and polyethylene," *Rheol Acta*, vol. 46, p. 153-159 (2006).

C. Gabriel et al., "Influence of molecular structure on rheological properties of polyethylenes," *Rheol Acta*, vol. 37, p. 7-20 (1998).

G. Schlatter et al., "Fourier Transform Rheology of Branched Polyethylene: Experiments and Models for Assessing the Macromolecular Architecture," *Macromolecules*, vol. 38, p. 6492-6544 (2005).

W. Frieseleben, "Über eine neue Fulven-Synthese [1]," *Angew Chem.*, vol. 75(12), p. 576 (1963).

L. Brandsma, Preparative Polar Organometallic Chemistry, Springer-Verlag, vol. 2, p. 133-142 (1992).

J. Michl, Editor, *Chemical Reviews*, vol. 100(4), p. 1169-1681 (2000).

L. Fieser et al., *Lehrbuch der Organischen Chemie*, Kapitel 33, p. 921-941, Weinheim (1957).

R. Halterman, "Synthesis and Applications of Chiral Cyclopentadienylmetal Complexes," *Chem. Rev.*, vol. 92, p. 965-994 (1992).

S. Strauss, "The Search for Larger and More Weakly Coordinating Anions," *Chem. Rev.*, vol. 93(3), p. 927-942 (1993).

M. Enders et al., "8-Quinolylcylopentadienyl, a Ligand with a Tailored Fit for Chelate Complexes," *Chem. Ber.*, vol. 129, p. 459-463 (1996).

J. Ewen et al., "Expanding the Scope of Metallocene Catalysis: Beyond Indenyl and Fluorenyl Derivatives," p. 150-169 (1999).

N. Furukawa et al., "Preparation of Pyridyl Grignard Reagents and Cross Coupling Reactions with Sulfoxides Bearing Azaheterocycles," *Tetrahedron Letters*, vol. 28(47), p. 5845-5848 (1987).

P. Jutzi et al., "Cyclopentadienyl compounds with nitrogen donors in the side-chain," *Journal of Organometallic Chemistry*, vol. 500, p. 175-185 (1995).

Kirk-Othmer, "Olefin Polymers (High Pressure Polyethylene); High Pressure (Low and Intermediate Density) Polyethylene;" *Encyclopedia of Chemical Technology*, vol. 16, p. 402-420 (1981).

Lettau, *Chemie der Heterocyclen, p. 17-27, 1st* edition, VEB, Weinheim (1979).

H. Brinzinger et al., "*ansa*-Metallocene derivatives—XVII. Racemic and *meso* diastereomers of group IV metallocene derivatives with symmetrically substituted, dimethylsilanediyl-bridged ligand frameworks. Crystal structure of R,S-$Me_2Si(3\text{-t-Bu-5-}MeC_5H_2)_2Zrcl_2$;" *Journal of Organometallic Chemistry*, vol. 369, p. 359-370 (1989).

M. Brookhart et al., "Highly Active Iron and Cobalt Catalysts for the Polymerization of Ethylene," *J. Am. Chem. Soc.*, vol. 120(16), p. 4049-4050 (1998).

V. Gibson et al., "Novel olefin polymerization catalysts based on iron and cobalt," *Chem. Commun.*, p. 849 (1998).

Theopold et al., "Constrained Geometry Chromium Catalysts for Olefin Polymerization" *Organometallics*, vol. 15, p. 5284-5286 (1996).

M. Blais et al., "Pendant Aminoalkyl-Substituted Monocyclopentadienyltitanium Compounds and Their Polymerization Behavior;" vol. 17(17), p. 3775-3783 (1998).

H. Münstedt et al., "Influence of molecular structure on rheological properties of polyethylenes; Part II. Elongational behavior," *Rheol Acta*, vol. 37, p. 21-29 (1998).

I. Vittorias et al., "Detection of Long-Chain Branching in Polylolefins via Fourier-Transform Rheology and Finite Element Simulations," *Macromol. Mat. Eng.*, p. 115-120 (2007).

G. Georgiou, "Stick-Slip Instability," *Polymer Processing Instabilities* edited by S. Hatzikiriakos & S. Migler, Dekker, NY, p. 161-206 (2005).

S. Wang et al., "Exploring molecular origins of sharkskin, partial slip, and slope change in flow curves of linear low density polyethylene," *J. Rheol.*, vol. 40(5), p. 875-898 (1996).

S. Wang et al., Stick-slip transition in capillary flow of linear polyethylene: 3. Surface conditions, *Rheol Acta*, vol. 36, p. 128-134 (1997).

Office Action from currently pending U.S. Appl. No. 10/538,540 with mail date Apr. 6, 2006.

Response and Amendment from currently pending U.S. Appl. No. 10/538,540 with mail date Oct. 6, 2006.

Office Action from currently pending U.S. Appl. No. 10/538,540 with mail date Jan. 19, 2007.

Response and Amendment from currently pending U.S. Appl. No. 10/538,540 with mail date Jul. 19, 2007.

Office Action from currently pending U.S. Appl. No. 10/538,540 with mail date Oct. 18, 2007.

Response and Amendment from currently pending U.S. Appl. No. 10/538,540 with mail date Apr. 18, 2008.

Office Action from currently pending U.S. Appl. No. 10/538,540 with mail date Jul. 23, 2008.

Response and Amendment from currently pending U.S. Appl. No. 10/538,540 with mail date Oct. 23, 2008.

Notice of Allowance from currently pending U.S. Appl. No. 10/538,540 with mail date Jan. 22, 2009.

Issue Notification from currently pending U.S. Appl. No. 10/538,540 with mail date Apr. 29, 2009.

Office Action from currently pending U.S. Appl. No. 10/539,242 with mail date Jul. 3, 2007.

Amendment from currently pending U.S. Appl. No. 10/539,242 with mail date Dec. 21, 2007.

Office Action from currently pending U.S. Appl. No. 10/539,242 with mail date Mar. 18, 2008.

RCE and Amendment from currently pending U.S. Appl. No. 10/539,242 with mail date Jun. 19, 2008.

Notice of Allowance from currently pending U.S. Appl. No. 10/539,242 with mail date Jul. 22, 2008.

RCE from currently pending U.S. Appl. No. 10/539,242 with mail date Oct. 17, 2008.

Notice of Allowance from currently pending U.S. Appl. No. 10/539,242 with mail date Dec. 2, 2008.

Issue Notification from currently pending U.S. Appl. No. 10/539,242 with mail date Mar. 4, 2009.

US 5,625,016, 04/1997, Schiffino et al. (withdrawn)

* cited by examiner

MONOCYCLOPENTADIENYL COMPLEXES

CROSS-REFERENCE TO RELATED APPLICATIONS

This application is a continuation of application Ser. No. 10/539,342, filed Jun. 16, 2005, now U.S. Pat. No. 7,541,473. This application entered the national stage in the U.S. based on international application PCT/EP03/14447, filed Dec. 18, 2003, and also claims the benefit of provisional U.S. Appl. No. 60/490,303, filed Jul. 25, 2003 and German application 10261109.2, filed Dec. 20, 2002.

The present invention relates to monocyclopentadienyl complexes in which the cyclopentadienyl system bears at least one unsubstituted, substituted or fused, heteroaromatic ring system bound via a specific bridge and to a catalyst system comprising at least one of the monocyclopentadienyl complexes, and also to processes for preparing the latter.

In addition, the invention relates to the use of the catalyst system for the polymerization or copolymerization of olefins and to a process for preparing polyolefins by polymerization or copolymerization of olefins in the presence of the catalyst system and to polymers obtainable in this way.

Many of the catalysts which are used for the polymerization of α-olefins are based on immobilized chromium oxides (cf. for example, Kirk-Othmer, "Encyclopedia of Chemical Technology", 1981, Vol. 16, p. 402). These generally give ethylene homopolymers and copolymers having high molecular weights, but are relatively insensitive to hydrogen and thus do not allow the molecular weight to be controlled in a simple manner. On the other hand, the use of bis(cyclopentadienyl)-chromium (U.S. Pat. No. 3,709,853), bis(indenyl) chromium or bis(fluorenyl)chromium (U.S. Pat. No. 4,015,059) which has been applied to an inorganic, oxidic support enables the molecular weight of polyethylene to be controlled in a simple fashion by addition of hydrogen.

As in the case of Ziegler-Natta systems, there is now also a search for chromium-based catalyst systems having a uniquely defined, active center, namely single side catalysts. The activity and copolymerization behavior of the catalyst and the properties of the polymers obtained therewith should be able to be altered in a simple manner by targeted variation of the ligand framework.

Thus, EP 0 742 046 claims constrained geometry complexes of elements of transition group 6, a specific process for preparing them (via metal tetraamides) and a process for preparing a polyolefin in the presence of such catalysts. Polymerization examples are not given. The ligand framework comprises an anionic donor which is linked to a cyclopentadienyl radical.

In Organomet. 1996, 15, 5284-5286, K. H. Theopold et al. describe an analogous {[(tert-butylamido)dimethylsilyl](tetramethylcyclopentadienyl)}chromium chloride complex for the polymerization of olefins. This complex selectively polymerizes ethylene. Comonomers such as hexene are not incorporated, and propene cannot be polymerized.

This disadvantage can be overcome by use of structurally similar systems. Thus, DE 197 10615 describes monocyclopentadienylchromium compounds which are substituted by donor ligands and by means of which propene, for example, can also be polymerized. The donor is from group 15 and is uncharged. The donor is bound to the cyclopentadienyl ring via a $(ZR_2)_n$ fragment, where R is hydrogen, alkyl or aryl, Z is an atom of group 14 and n≧1. In DE 196 30 580, Z=carbon in combination with an amine donor is specifically claimed.

WO 96/13529 describes reduced transition metal complexes of metals of groups 4 to 6 of the Periodic Table with polydentate monoanionic ligands. These include cyclopentadienyl ligands containing a donor function. The examples are restricted to titanium compounds.

There are also ligand systems in which the donor group is linked rigidly to the cyclopentadienyl radical. Such ligand systems and their metal complexes are summarized by, for example, P. Jutzi and U. Siemeling in J. Orgmet. Chem. (1995), 500, 175-185, Section 3. In Chem. Ber. (1996), 129, 459-463, M. Enders et al. describe 8-quinolyl-substituted cyclopentadienyl ligands and their titanium trichloride and zirconium trichloride complexes. 2-Picolylcyclopentadienyltitanium trichloride in combination with MAO has been used by M. Blais, J. Chien and M. Rausch in Organomet. (1998), 17 (17) 3775-3783, for the polymerization of olefins.

WO 01/92346 discloses cyclopentadienyl complexes-of elements of groups 4-6 of the Periodic. Table of the Elements, in which a dihydrocarbyl-Y group is bound to the cyclopentadienyl system, where Y is an element of group 14 of the Periodic Table of the Elements which bears particular Lewis bases.

It is an object of the invention to find further transition metal complexes based on cyclopentadienyl ligands having a bridged donor which are suitable for the polymerization of olefins. A further object of the invention is to find an advantageous process for preparing such complexes.

We have found that this object is achieved by monocyclopentadienyl complexes which comprise the structural feature of the formula $(Cp)(-Z-A)_mM$ (I), where the variables have the following meanings:

Cp is a cyclopentadienyl system,

Z is a bridge between A and Cp of the formula,

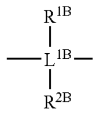

where $L^{1B}$ are each, independently of one another, carbon or silicon preferably carbon, $R^{1B}$ is $C_2$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{3B}_3$, where the organic radical $R^{1B}$ may also be substituted by halogens and $R^{1B}$ and A may also be joined to form a five- or six-membered ring, $R^{2B}$ is hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{3B}_3$, where the organic radical $R^{2B}$ may also be substituted by halogens and $R^{2B}$ and A may also be joined to form a five- or six-membered ring and $R^{3B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{3B}$ may also be joined to form a five- or six-membered ring, A is an unsubstituted, substituted or fused, heteroaromatic ring system, M is a metal selected from the group consisting of titanium in the oxidation state 3, vanadium, chromium, molybdenum and tungsten and m is1, 2 or 3.

We have also found a catalyst system comprising the monocyclopentadienyl complexes of the present invention, the use of the monocyclopentadienyl complexes or the catalyst system for the polymerization or copolymerization of olefins and a process for preparing polyolefins by polymerization or copolymerization of olefins in the presence of the monocyclopentadienyl complex or the catalyst system and have also found polymers obtainable therefrom.

The monocyclopentadienyl complexes of the present invention comprise the structural element of the formula (Cp)(-Z-A)$_m$M (I), where the variables are as defined above. Further ligands may therefore be bound to the metal atom M. The number of further ligands depends, for example, on the oxidation state of the metal atom. Possible ligands do not include further cyclopentadienyl systems. Suitable ligands include monoanionic and dianionic ligands as described, for example, for X. Furthermore, Lewis bases such as amines, ethers, ketones, aldehydes, esters, sulfides or phosphines can also be bound to the metal center M.

Cp is a cyclopentadienyl system which may have any desired substitution pattern and/or be fused with one or more aromatic, aliphatic, heterocyclic or heteroaromatic rings, with 1, 2 or 3 substituents, preferably 1 substituent, being the group -Z-A. The basic cyclopentadienyl skeleton itself is a $C_5$ ring system having 6π electrons in which one of the carbon atoms may also be replaced by nitrogen or phosphorus, preferably phosphorus. Preference is given to using $C_5$ ring systems without replacement by a heteroatom. A heteroaromatic which contains at least one atom from the group consisting of N, P, O and S or an aromatic can, for example, be fused onto this basic cyclopentadienyl skeleton. In the present context, fused onto means that the heterocycle and the basic cylopentadienyl skeleton share two atoms, preferably carbon atoms. Preference is given to cyclopentadienyl systems Cp of the formula (II)

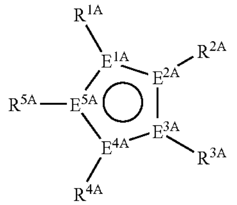
(II)

where the variables have the following meanings:

$E^{1A}$-$E^{5A}$ are each carbon or not more than one $E^{1A}$ to $E^{5A}$ is phosphorus, $R^{1A}$-$R^{5A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{6A}_2$, $N(SiR^{6A}_3)_2$, $OR^{6A}$, $OSiR^{6A}_3$, $SiR^{6A}_3$, $BR^{6A}_2$, where the organic radicals $R^{1A}$-$R^{5A}$ may also be substituted by halogens and two vicinal radicals $R^{1A}$-$R^{5A}$ may also be joined to form a five- or six-membered ring, and/or two vicinal radicals $R^{1A}$-$R^{5A}$ are joined to form a heterocycle which contains at least one atom from the group consisting of N, P, O and S, with 1, 2 or 3 substituents $R^{1A}$-$R^{5A}$ preferably one substituent $R^{1A}$-$R^{5A}$, being a -Z-A group and $R^{6A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{6A}$ may also be joined to form a five- or six-membered ring.

In preferred cyclopentadienyl systems Cp, all $E^{1A}$ to $E^{5A}$ are carbon.

Two vicinal radicals $R^{1A}$-$R^{5A}$ together with the $E^{1A}$-$E^{5A}$ bearing them may form a heterocycle, preferably a heteroaromatic, containing at least one atom from the group consisting of nitrogen, phosphorus, oxygen and sulfur, particularly preferably nitrogen and/or sulfur, with the $E^{1A}$-$E^{5A}$ present in the heterocycle or heteroaromatic preferably being carbon atoms. Preference is given to heterocycles and heteroaromatics having a ring size of 5 or 6 atoms. Examples of 5-membered heterocycles which may have from one to four nitrogen atoms and/or a sulfur or oxygen atom in addition to carbon atoms as ring atoms are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole and 1,2,4-triazole. Examples of 6-membered heteroaryl groups which may contain from one to four nitrogen atoms and/or a phosphorus atom are pyridine, phosphabenzene, pyridazine, pyrimidine, pyrazine, 1,3,5-triazine, 1,2,4-triazine and 1,2,3-triazine. The 5-membered and 6-membered heterocycles may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine, dialkylamido, alkylarylamido, diarylamido, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chroman, benzopyran, quinoline, isoquinoline, cinnoline, phthalazine, quinazoline, quinoxaline, 1,10-phenanthroline and quinolizine. Naming and numbering of the heterocycles has been taken from Lettau, Chemie der Heterocyclen, 1st edition, VEB, Weinheim 1979. The heterocycles/heteroaromatics are preferably fused with the basic cyclopentadienyl skeleton via a C—C double bond of the heterocycle/heteroaromatic. Heterocycles/heteroaromatics having one heteroatom are preferably 2,3- or b-fused.

Examples of cyclopentadienyl systems Cp having a fused-on heterocycle are thiapentalene, 2-methylthiapentalene, 2-ethylthiapentalene, 2-isopropylthiapentalene, 2-n-butylthiapentalene, 2-tert-butylthiapentalene, 2-trimethylsilylthiapentalene, 2-phenylthiapentalene, 2-naphthylthiapentalene, 3-methylthiapentalene, 4-phenyl-2,6-dimethyl-1-thiapentalene, 4-phenyl-2,6-diethyl-1-thiapentalene, 4-phenyl-2,6-diisopropyl-1-thiapentalene, 4-phenyl-2,6-di-n-butyl -1-thiapentalene, 4-phenyl-2,6-ditrimethylsilyl-1-thiapentalene, azapentalene, 2-methylazapentalene, 2-ethylazapentalene, 2-isopropylazapentalene, 2-n-butylazapentalene, 2-trimethylsilylazapentalene, 2-phenylazapentalene, 2-naphthylazapentalene, 1-phenyl-2,5-dimethyl-1-azapentalene, 1-phenyl-2,5-diethyl-1-azapentalene, 1-phenyl-2,5-di-n-butyl-1-azapentalene, 1-phenyl-2,5-di-tert-butyl-1-azapentalene, 1-phenyl-2,5-ditrimethylsilyl-1-azapentalene, 1-tert-butyl-2,5-dimethyl-1-azapentalene, oxapentalene, phosphapentalene, 1-phenyl-2,5-dimethyl-1-phosphapentalene, 1-phenyl-2,5-diethyl-1-phosphapentalene, 1-phenyl-2,5-di-n-butyl-1-phosphapentalene, 1-phenyl-2,5-di-tert-butyl-1-phosphapentalene, 1-phenyl-2,5-ditrimethylsilyl-1-phosphapentalene, 1-methyl-2,5-dimethyl-1-phosphapentalene, 1-tert-butyl-2,5-dimethyl-1-phosphapentalene, 7-cyclopenta[1,2]thieno[3,4]-cyclopentadiene and 7-cyclopenta[1,2]pyrrolo[3,4]cyclopentadiene.

In further preferred cyclopentadienyl systems Cp, four of the radicals $R^{1A}$-$R^{5A}$, i.e. two pairs of vicinal radicals, form two heterocycles, in particular heteroaromatics. The heterocyclic systems are the same as those described in more detail above. Examples of cyclopentadienyl systems Cp having two fused-on heterocycles are 7-cyclopentadithiophene, 7-cyclopentadipyrrole and 7-cyclopentadiphosphole.

The synthesis of such cyclopentadienyl systems having a fused-on heterocycle is described, for example, in the above-mentioned WO 98122486. In "metalorganic catalysts for synthesis and polymerisation", Spring Verlag 1999, p. 150 ff, Ewen et al. describe further syntheses of these cyclopentadienyl systems.

Variation of the substituents $R^{1A}$-$R^{5A}$ can likewise exert an influence on the polymerization behavior of the metal complexes. The ability of the olefins to be polymerized to gain access to the metal atom M can be influenced by the number and type of substituents. This makes it possible to modify the activity and selectivity of the catalyst in respect of various monomers, in particular bulky monomers. Since the substituents can also have an influence on the rate of termination reactions of the growing polymer chain, the molecular weight of the polymers formed can also be altered in this way. The chemical structure of the substituents $R^{1A}$ to $R^{5A}$ can therefore be varied within a wide range in order to achieve the desired results and to give a tailored catalyst system. Examples of suitable carboorganic substituents $R^{1A}$-$R^{5A}$ are the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl,.cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, and arylalkyl which may bear further alkyl groups as substituents, e.g. benzyl, o-, m-, p-methylbenzyl, 1- or 2-ethylphenyl, where two radicals $R^{1A}$ to $R^{5A}$ may also be joined to form a 5- or 6-membered ring and the organic radicals $R^{1A}$-$R^{5A}$ may also be substituted by halogens, e.g. fluorine, chlorine or bromine. Furthermore, $R^{1A}$-$R^{5A}$ can also be amino or alkoxy, for example dimethylamino, N-pyrrolidinyl, picolinyl, methoxy, ethoxy or isopropoxy. In organosilicon substituents $SiR^{6A}_3$, possible radicals $R^{6A}$ are the same ones which are mentioned in more detail above for $R^{1A}$-$R^{5A}$ and it is also possible for two radicals $R^{6A}$ to be joined to form a 5- or 6-membered ring, so that examples of suitable $SiR^{6A}_3$ substituents are trimethylsilyl, triethylsilyl, butyldimethylsilyl, tributylsilyl, tri-tert-butylsilyl, triallylsilyl, triphenylsilyl and dimethylphenylsilyl. These $SiR^{6A}_3$ radicals may also be bound to the cyclopentadienyl skeleton via an oxygen or nitrogen atom, for example trimethylsilyloxy, triethylsilyloxy, butyldimethylsilyloxy, tributylsilyloxy or tri-tert-butylsilyloxy. Preferred radicals $R^{1A}$-$R^{5A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl and anthranyl. As organosilicon substituents, particular preference is given to trialkylsilyl groups having from 1 to 10 carbon atoms in the alkyl radical, in particular trimethylsilyl groups.

Examples of such cyclopentadienyl systems (without the group -Z-A, which is preferably in the 1 position) are 3-methylcyclopentadienyl, 3-ethylcyclopentadienyl, 3-isopropylcyclopentadienyl, 3-tert-butylcyclopentadienyl, dialkylcyclopentadienyl, e.g. tetrahydroindenyl, 2,4-dimethylcyclopentadienyl or 3-methyl-5-tert-butylcyclopentadienyl, trialkylcyclopentadienyl, e.g. 2,3,5-trimethylcyclopentadienyl, and tetraalkylcyclopentadienyl, e.g. 2,3,4,5-tetramethylcyclopentadienyl.

Preference is also given to compounds in which two vicinal radicals $R^{1A}$-$R^{5A}$ form a cyclic fused ring system, i.e. together with the basic $E^{1A}$-$E^{5A}$ skeleton, preferably a $C_5$-cyclopentadienyl skeleton, form, for example, an unsubstituted or substituted indenyl, benzindenyl, phenanthrenyl, fluorenyl or tetrahydroindenyl system, for example indenyl, 2-methylindenyl, 2-ethylindenyl, 2-isopropylindenyl, 3-methylindenyl, benzindenyl or 2-methylbenzindenyl.

The fused ring system may bear further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part, $NR^{6A}_2$, $N(SiR^{6A}_3)_2$, $OR^{6A}$, $OSiR^{6A}_3$ or $SiR^{6A}_3$, e.g. 4-methylindenyl, 4-ethylindenyl, 4-isopropylindenyl, 5-methylindenyl, 4-phenylindenyl, 5-methyl-4-phenylindenyl, 2-methyl-4-phenylindenyl or 4-naphthylindenyl.

Preferred substituents $R^{1A}$-$R^{5A}$ which do not form -Z-A are the above-described carboorganic substituents and the carboorganic substituents which form a fused ring system, in particular their preferred embodiments.

m can be 1, 2 or 3, i.e. 1, 2 or 3 radicals. $R^{1A}$-$R^{5A}$ are -Z-A; in the case of 2 or 3 -Z-A radicals being present, these can be identical or different. Preference is given to only one of the radicals $R^{1A}$-$R^{5A}$ being -Z-A (m=1).

Like metallocenes, the monocyclopentadienyl complexes of the present invention can be chiral. Thus, one of the substituents $R^{1A}$-$R^{5A}$ on the basic cyclopentadienyl skeleton can have one or more chiral centers, or else the cyclopentadienyl system Cp can itself be enantiotopic so that chirality is in use only when it is bound to the transition metal M (for the formalisms concerning chirality in cyclopentadienyl compounds, see R. Halterman, Chem. Rev. 92, (1992), 965-994).

Z is preferably a $CR^{1B}R^{2B}$ group.

Possible carboorganic substituents $R^{1B}$-$R^{2B}$ on the link Z are, for example the following: $C_2$-$C_{20}$-alkyl which may be linear or branched, e.g. ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituents, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where $R^{2B}$ may also be methyl or hydrogen and the organic radicals $R^{1B}$-$R^{2B}$ may also be substituted by halogens, e.g. fluorine, chlorine or bromine, or alkyl or aryl.

Possible radicals $R^{3B}$ in organosilicon substituents $SiR^{3B}_3$ are the same radicals which have been described in more detail above for $R^{2B}$, and two radicals $R^{3B}$ may also be joined to form a 5- or 6-membered ring, so that examples of suitable substituents $SiR^{3B}_3$ are trimethylsilyl, triethylsilyl, butyldimethylsilyl, tributylsilyl, tri-tert-butylsilyl, triallylsilyl, triphenylsilyl and dimethylphenylsilyl.

The radicals $R^{1B}$ and $R^{2B}$ may be identical or different. Preference is given to $R^{1B}$ and $R^{2B}$ being different, so that $L^{1B}$ is a chiral center.

Preferred radicals $R^{1B}$ are ethyl, n-propyl, isopropyl, n-butyl, isobutyl, tert-butyl, n-pentyl, n-hexyl, n-heptyl, n-octyl, benzyl, phenyl, ortho-dialkyl- or ortho-dichloro-substituted phenyls, trialkyl- or trichloro-substituted phenyls, naphthyl, biphenyl and anthranyl, while $R^{2B}$ is at the same tome hydrogen or methyl, in particular hydrogen. Z is particularly preferably a —$CH(C_6H_5)$— group.

In another preferred embodiment $R^{1B}$ is an olefinic unsaturated $C_2$-$C_{20}$-radical, wherein the double bond is preferably a terminal vinyl group, preferably a ω-alkenyl radical, wherein the ω-alkenyl radical with a terminal vinyl group. Preferred radicals $R^{1B}$ in this embodiment are 4-penten-1-yl, 5-hexen-1-yl, 6-hepten-1-yl and 7-octen-1-yl. These kind of radicals lead in the ethylene copolymerisation reactions to copolymers with a higher molecular weight than the ethylene homopolymers in the respective ethylene homopolymerisations.

The bridge Z between the cyclopentadienyl system Cp and the heteroaromatic A is an organic, preferably divalent, bridge comprising sterically substituted carbon and/or silicon units. Z can be bound to the basic cyclopentadienyl skeleton or be bound to the heterocycle or the fused-on ring of the cyclopentadienyl system. Z is preferably bound to the basic cyclopentadienyl skeleton. The activity of the catalyst can be influenced by the change in the length of the link between the cyclopentadienyl system and A. Z is particularly preferably bound both to the fused-on heterocycle or fused-on aromatic and to the basic cyclopentadienyl framework. If the heterocycle or aromatic is fused on in the 2,3 position of the cyclopentadienyl skeleton, Z is preferably located in the 1 or 4 position of the cyclopentadienyl skeleton.

A is an unsubstituted, substituted or fused heteroaromatic ring system which can contain heteroatoms from the group consisting of oxygen, sulfur, nitrogen and phosphorus in addition to the ring carbons. Examples of 5-membered heteroaryl groups which, in addition to carbon atoms, contain from one to four nitrogen atoms or from one to three nitrogen atoms and/or a sulfur or oxygen atom as ring atoms are 2-furyl, 2-thienyl, 2-pyrrolyl, 3-isoxazolyl, 6-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl and 1,2,4-triazol-3-yl. Examples of 6-membered heteroaryl groups which can contain from one to four nitrogen atoms and/or a phosphorus atom are 2-pyridinyl, 2-phosphabenzolyl 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl.

A can bind to the metal M either intermolecularly or intramolecularly. A is preferably bound intramolecularly to M. The synthesis of the compound in which A is bound to the cyclopentadienyl ring can be carried out, for example, by methods analogous to those of M. Enders et al. in Chem. Ber. (1996), 129, 459-463 and P. Jutzi and U. Siemeling in J. Orgmet. Chem. (1995), 500, 175-185.

Among these heteroaromatic systems, particular preference is given to unsubstituted, substituted and/or fused 6-membered heteroaromatics having 1, 2, 3, 4 or 5 nitrogen atoms in the heteroaromatic moiety to which Z is bound, in particular 2-pyridyl or 2-quinolyl. A is therefore preferably a group of the formula (III)

(III)

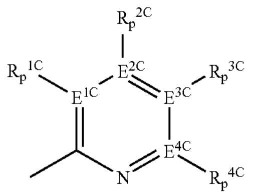

where $E^{1C}$-$E^{4C}$ are each carbon or nitrogen, $R^{1C}$-$R^{4C}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{5C}_3$, where the organic radicals $R^{1C}$-$R^{4C}$ may also be substituted by halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ and two vicinal radicals $R^{1C}$-$R^{4C}$ or $R^{1C}$ and Z may also be joined to form a five- or six-membered ring, $R^{5C}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{5C}$ may also be joined to form a five- or six-membered ring and p is 0 when $E^{1C}$-$E^{4C}$ is nitrogen and is 1 when $E^{1C}$-$E^{4C}$ is carbon.

In particular, 0 or 1 $E^{1C}$-$E^{4C}$ is nitrogen and the others are carbon. A is particularly preferably a 2-pyridyl, 6-methyl-2-pyridyl, 4-methyl-2-pyridyl, 5-methyl -2-pyridyl, 5-ethyl-2-pyridyl, 4,6dimethyl-2-pyridyl; 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethyl-2-pyrazinyl, 3,5,6-trimethyl-2-pyrazinyl, 2-quinolyl, 4-methyl-2quinolyl, 6-methyl-2-quinolyl, 7-methyl-2-quinolyl, 2-quinoxalyl or 3-methyl-2-quinoxalyl.

In preferred monocyclopentadienyl complexes, the cyclopentadienyl system Cp and -Z-A form a ligand (Cp-Z-A) of the formula IV:

(IV)

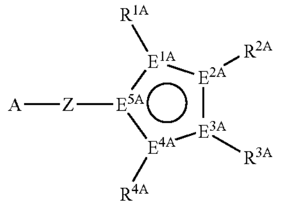

where the variables A, Z, $E^{1A}$ to $E^{5A}$ and $R^{6A}$ are as defined above and their preferred embodiments are also preferred here and $R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{6A}_2$, $N(SiR^{6A}_3)_2$, $OR^{6A}$, $OSiR^{6A}_3$, $SiR^{6A}_3$, $BR^{6A}_2$, where the organic radicals $R^{1A}$-$R^{4A}$ may also be substituted by halogens and two vicinal radicals $R^{1A}$-$R^{4A}$ may also be joined to form a five- or six-membered ring, and/or two vicinal radicals $R^{1A}$-$R^{4A}$ are joined to form a heterocycle which contains at least one atom from the group consisting of N, P, O and S.

The embodiments and preferred embodiments described above likewise apply to the $R^{1A}$-$R^{4A}$ described here.

Among these preferred ligands (Cp-Z-A), particular preference is given to those of the formula V:

(V)

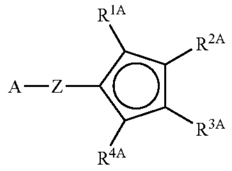

where the variables A, Z and $R^{6A}$ are as defined above and their preferred embodiments are also preferred here and $R^{1A}R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{6A}_2$, $N(SiR^{6A}_3)_2$, $OR^6$, $OSiR^{6A}_3$, $SiR^{6A}_3$, $BR^{6A}_2$, where the organic radicals $R^{1A}$-$R^{4A}$ may also be substituted by halogens and two vicinal radicals $R^{1A}$-$R^{4A}$ may also be joined to form a five- or six-membered ring, and/or two vicinal radicals $R^{1A}$-$R^{4A}$ are joined to form a heterocycle which contains at least one atom from the group consisting of N, P, O and S.

The embodiments and preferred embodiments described above likewise apply to the $R^{1A}$-$R^{4A}$ described here.

In particular, the monocyclopentadienyl complex contains the ligand (Cp-Z-A) of the formula IV or V in the following preferred embodiment:

Z is —$CHR^{1B}$—, in particular —$CH(C_6H_5)$—,

A is (III)

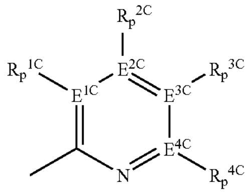

where $E^{1C}$-$E^{4C}$ are each carbon or nitrogen, $R^{1C}$-$R^{4C}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{5C}_3$, where the organic radicals $R^{1C}$-$R^{4C}$ may also be substituted by halogens or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ and two vicinal radicals $R^{1C}$-$R^{4C}$ or $R^{1C}$ and Z may also be joined to form a five- or six-membered ring, $R^{5C}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{5C}$ may also be joined to form a five- or six-membered ring and p is 0 when $E^{1C}$-$E^{4C}$ is nitrogen and is 1 when $E^{1C}$-$E^{4C}$ is carbon.

M is a metal selected from the group consisting of titanium in the oxidation state 3, vanadium, chromium, molybdenum and tungsten, preferably titanium in the oxidation state 3 and chromium. Particular preference is given to chromium in the oxidation states 2, 3 and 4, in particular 3. The metal complexes, in particular the chromium complexes, can be obtained in a simple manner by reacting the corresponding metal salts, e.g. metal chlorides, with the ligand anion (e.g. by methods analogous to the examples in DE 197 10615).

Among the monocyclopentadienyl complexes of the present invention, preference is given to those of the formula $(Cp)(\text{-}Z\text{-}A)_mMX_k$ (VI), where the variables Cp, Z, A, m and M are as defined above and their preferred embodiments are also preferred here and:

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$ or a bulky noncoordinating anion, $R^1$-$R^2$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^3_3$, where the organic radicals $R^1$-$R^2$ may also be substituted by halogens or nitrogen- and oxygen-containing groups and two radicals $R^1$-$R^2$ may also be joined to form a five- or six-membered ring, $R^3$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^3$ may also be joined to form a five- or six-membered ring and k is 1, 2, or 3.

The embodiments and preferred embodiments of Cp, Z, A, m and M described above also apply individually and in combination to these preferred monocyclopentadienyl complexes.

The ligands X are determined, for example, by the choice of the appropriate metal starting compounds used for the synthesis of the monocyclopentadienyl complexes, but can also be altered afterwards. Possible ligands X are, in particular, halogens such as fluorine, chlorine, bromine or iodine, in particular chlorine. Alkyl radicals such as methyl, ethyl, propyl, butyl, vinyl, allyl, phenyl or benzyl are also advantageous ligands X. Further ligands X are, purely by way of example without being exhaustive, trifluoroacetate, $BF_4^-$, $PF_6^-$ and weakly coordinating or noncoordinating anions (cf., for example, S. Strauss in Chem. Rev. 1993, 93, 927-942), e.g. $B(C_6F_5)_4^-$.

Amides, alkoxides, sulfonates, carboxylates and β-diketonates are also particularly useful ligands X. Variation of the radicals $R^1$ and $R^2$ enables fine adjustments to, for example, physical properties such as solubility to be made. Examples of possible carboorganic substituents $R^1$-$R^2$ are the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be in internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups and/or N— or O-containing radicals as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl, and arylalkyl which may bear further alkyl groups as substituents, e.g. benzyl, o-, m-, p-methylbenzyl, 1- or 2-ethylphenyl, where $R^1$ may also be joined to $R^2$ to form a 5- or 6-membered ring and the organic radicals $R^1$-$R^2$ may also be substituted by halogens such as fluorine, chlorine or bromine. Possible radicals $R^3$ in organosilicon substituents $SiR^3_3$ are the same radicals as have been described in more detail above for $R^1$-$R^2$, where two $R^3$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl and also vinyl, allyl, benzyl and phenyl as radicals $R^1$ and $R^2$. Some of these substituted ligands X are very particularly preferably used since they are obtainable from cheap and readily available starting materials. A particularly preferred embodiment is therefore one in which X is dimethylamide, methoxide, ethoxide, isopropoxide, phenoxide, naphthoxide, triflate, p-toluenesulfonate, acetate or acetylacetonate.

The number k of the ligands X depends on the oxidation state of the transition metal M. The number k can therefore not be given in general terms. The oxidation state of the transition metals M in catalytically active complexes is usually known to those skilled in the art. Chromium, molybdenum and tungsten are very probably present in the oxidation state +3, vanadium in the oxidation state +3 or +4. However, it is also possible to use complexes whose oxidation state does not correspond to that of the active catalyst. Such complexes can then be appropriately reduced or oxidized by suitable activators. Preference is given to using chromium complexes in the oxidation state +3 and titanium complexes in the oxidation state 3.

Furthermore, we have found a process for preparing cyclopentadienyl system anions of the formula (VII), (VII)

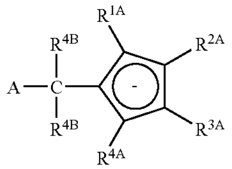

where the variables have the following meanings:

$R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{6A}_2$, $N(SiR^{6A}_3)_2$, $OR^{6A}$, $OSiR^{6A}_3$, $SiR^{6A}_3$ where the organic radicals $R^{1A}$-$R^{4A}$ may also be substituted by halogens and two vicinal radicals $R^{1A}$-$R^{4A}$ may also be joined to form a five- or six-membered ring, and/or two vicinal radicals $R^{1A}$-$R^{4A}$ are joined to form a heterocycle which contains at least one atom from the group consisting of N, P, O and S, $R^{6A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{6A}$ may also be joined to form a five- or six-membered ring, A is an unsubstituted, substituted or fused, heteroaromatic ring system, $R^{4B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{3B}_3$, where the organic radicals $R^{4B}$ may also be substituted by halogens and two geminal or vicinal radicals $R^{4B}$ may also be joined to form a five- or six-membered ring and $R^{3B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{3B}$ may also be joined to form a five- or six-membered ring, which comprises the step a) or a'), where, in step a), an $A^-$ anion is reacted with a fulvene of the formula (VIIIa)

or, (VIIIa)

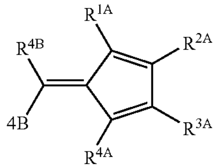

in step a'), an organometallic compound $R^{4B}M^BX^B_b$ where $M^B$ is a metal of group 1 or 2 of the Periodic Table of the Elements, $X^B$ is halogen, $C_1$-$C_{10}$-alkyl, alkoxy having from 1 to 20 carbon atoms in the alkyl part and/or from 6 to 20 carbon atoms in the aryl part, or $R^{2B}$ and b is 0 when $M^B$ is a metal of group 1 of the Periodic Table of the Elements and is 1 when $M^B$ is a metal of group 2 of the Periodic Table of the Elements, is reacted with a fulvene of the formula (VIIIb):

(VIIIb)

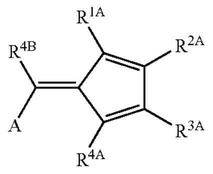

where the other variables are in each case as defined above.

The variables and their preferred embodiments have been described above.

Fulvenes have been known for a long time and can be prepared, for example, as described by Frelesleben, Angew. Chem. 75 (1963), p. 576. Preference is given to one of the substituents $R^{4B}$ in fulvene (VIIIa) being as defined for $R^{1B}$ and the other being as defined for $R^{2B}$ or both $R^{4B}$ in fulvene (VIIIa) being as defined for $R^{2B}$. $R^{4B}$ in fulvene (VIIIb) is preferably as defined for $R^{2B}$, in particular hydrogen.

The cyclopentadienyl system anion (VII) has the cation of the $A^-$ anion or of $M^BR^{4B}X^B_b$ as countercation. This is generally a metal of group 1 or 2 of the Periodic Table of the Elements, which may bear further ligands. Particular preference is given to lithium, sodium or potassium cations which may also bear uncharged ligands such as amines or ethers and magnesium chloride and magnesium bromide cations which may likewise bear further uncharged ligands, in particular lithium, magnesium chloride and magnesium bromide cations.

In $M^BR^{4B}X^B_b$, $R^{4B}$ is preferably $R^{1B}$. Such compounds are commercially available from FlukaAldrich or can be obtained, for example, by reacting the corresponding $R^{2B}$ halide with the metal $M^B$. Particular preference is given to lithium alkyls having a $C_1$-$C_{20}$-alkyl group, in particular a $C_1$-$C_8$-alkyl group.

The anion $A^-$ is usually obtained by metal-halogen exchange in the reaction of A halide with a metal alkyl compound containing a metal of groups 1 or 2, in particular lithium, magnesium chloride or magnesium bromide cations. Examples of suitable metal alkyl compounds are lithium alkyls, magnesium alkyls, magnesium (alkyl) halides, or mixtures thereof. The molar ratio of metal alkyl compound to A halide is usually in the range from 0.4:1 to 100:1, preferably in the range from 0.9:1 to 10:1 and particularly preferably from 0.95:1 to 1.1:1. Examples of such reactions have been described, for example, by Furukawa et al. in Tet. Lett. 28 (1987), 5845.

As solvents for the reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at from −100 to +160° C., in particular from −80 to 100° C. At temperatures above 40° C., preference is given to using aromatic or aliphatic solvents which do not contain any ether, or contain only a small proportion of ethers, as solvent.

The unsubstituted, substituted or fused, heteroaromatic ring system A is as defined above. The radicals $R^{1B}$ and $R^{2B}$ and their preferred embodiments have likewise been described above. The negative charge on the anion $A^-$ is preferably located on a carbon of $A^-$ adjacent to a heteroatom of $A^-$, in particular a nitrogen atom if one is present in $A^-$. A is preferably 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl, 2-pyridinyl, 2-phosphabenzenyl, 3-pyridazinyl, 2-pyrimidinyl, 4-pyrimidinyl, 2-pyrazinyl, 1,3,5-triazin-2-yl, 1,2,4-triazin-3-yl, 1,2,4-triazin-5-yl, 1,2,4-triazin-6-yl, 2-indolyl, 7-indolyl, 2-coumaronyl, 7-coumaronyl, 2-thionaphthenyl, 7-thionaphthenyl, 3-indazolyl, 7-indazolyl, 2-benzimidazolyl or 7-benzimidazolyl, 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl.

The $A^-$ anion is preferably a group of the formula (IIIa)

(IIIa)

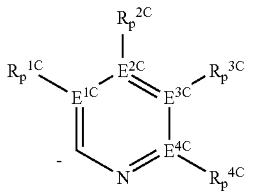

where the variables have the following meanings:

$E^{1C}$-$E^{4C}$ are each carbon or nitrogen, $R^{1C}$-$R^{4C}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{5C}_3$, where the organic radicals $R^{1C}$-$R^{4C}$ may also be substituted by halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ and two vicinal radicals $R^{1C}$-$R^{4C}$ may also be joined to form a five- or six-membered ring, $R^{5C}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{5C}$ may also be joined to form a five- or six-membered ring and p is 0 when $E^{1C}$-$E^{4C}$ is nitrogen and is 1 when $E^{1C}$-$E^{4C}$ is carbon.

In particular, 0 or 1 $E^{1C}$-$E^{4C}$ is nitrogen and the others are carbon. Particularly preferred $A^-$ systems are 2-pyridinyl, 3-pyridazinyl, 2-pyrimidinyl, 4-pyrimidinyl, 2-pyrazinyl, 2-quinolyl, 3-cinnolyl, 2-quinazolyl or 4-quinazolyl.

The $A^-$ anion formed after metal-halogen exchange can be isolated or preferably be reacted without further isolation with the fulvene (VIIIa). As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The deprotonation can be carried out at from −100 to +160° C., preferably from −80 to 100° C. and particularly preferably from 0 to 60° C. At temperatures above 40° C., preference is given to using aromatic or aliphatic solvents which contain no ether, or only a small proportion of ethers, as solvent.

The cyclopentadienyl system anion (VII) obtained in this way can then be reacted further with the appropriate transition metal compound, e.g. chromium trichloride tris(tetrahydrofuran), to give the corresponding monocyclopentadienyl complex (A).

Furthermore, we have found a process for preparing cyclopentadiene systems of the formula (VIIa), (VIIa)

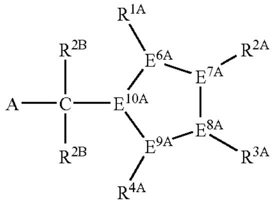

where the variables have the following meanings:

$E^{6A}$-$E^{10A}$ are each carbon, where in each case four adjacent $E^{6A}$-$E^{10A}$ form a conjugated diene system and the remaining $E^{6A}$-$E^{10A}$ additionally bears a hydrogen atom, $R^{1A}$-$R^{4A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{6A}_2$, $N(SiR^{6A}_3)_2$, $OR^{6A}$, $OSiR^{6A}_3$, $SiR^{6A}_3$, where the organic radicals $R^{1A}$-$R^{4A}$ may also be substituted by halogens and two vicinal radicals $R^{1A}$-$R^{4A}$ may also be joined to form a five- or six-membered ring, and/or two vicinal radicals $R^{1A}$-$R^{4A}$ are joined to form a heterocycle which contains at least one atom from the group consisting of N, P, O and S, $R^{6A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{6A}$ may also be joined to form a five- or six-membered ring, A is an unsubstituted, substituted or fused, heteroaromatic ring system, $R^{2B}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{3B}_3$, where the organic radicals $R^{2B}$ may also be substituted by halogens and $R^{2B}$ and A may also be joined to form a five- or six-membered ring, $R^{3B}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{3B}$ may also be joined to form a five- or six-membered ring, which comprises the following step:

a") reaction of an A-$CR^{2B}R^{2B-}$ anion, in particular an A-$CR^{1B}R^{2B-}$ anion, with a cyclopentenone system of the formula (IX)

(IX)

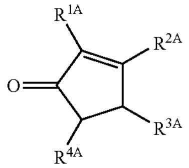

where the variables are as defined above.

The variables and their preferred embodiments have been described above and also apply in this process. Preference is given to one $R^{2B}$ of the A-$CR^{2B}R^{2B-}$ anion and thus in formula (VIIa) being as defined for $R^{1B}$.

The cation of the A-$CR^{2B}R^{2B-}$ anion and in particular the A-$CR^{1B}R^{2B-}$ anion, is generally a metal of group 1 or 2 of the Periodic Table of the Elements, which may bear further ligands. Particular preference is given to lithium, sodium or potassium cations which may also bear uncharged ligands such as amines or ethers and magnesium chloride and magnesium bromide cations which may likewise bear further uncharged ligands.

The A-$CR^{2B}R^{2B-}$ anion, in particular the A-$CR^{1B}R^{2B-}$ anion, is usually obtained by deprotonation of A-$CR^{2B}R^{2B}H$, in particular A-$CR^{1B}R^{2B}H$. This can be achieved using strong bases such as lithium alkyls, sodium hydride, sodium amides, sodium alkoxides, sodium alkyls, potassium hydride, potassium amides, potassium alkoxides, potassium alkyls, magnesium alkyls, magnesium (alkyl) halides, or mixtures thereof. The molar ratio of base to A-$CR^{2B}R^{2B}H$ is usually in the range from 0.4:1 to 100:1, preferably in the range from 0.9:1 to 10:1 and particularly preferably from 0.95:1 to 1.1:1. Examples of such deprotonations are described in L. Brandsma, Preparative polar organometallic chemistry 2, pp. 133-142.

As solvents in the deprotonation step, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The deprotonation can be carried out at from −100 to +160° C., in particular from −80 to 100° C. At temperatures above 40° C., preference is given to using aromatic or aliphatic solvents which contain no ether, or contain only a small proportion of ethers, as solvent.

The unsubstituted, substituted or fused, heteroaromatic ring system A is as defined above and bears a $CR^{2B}R^{2B}H$ group, in particular a $CR^{1B}R^{2B}H$ group. The radicals $R^{1B}$ and $R^{2B}$ and their preferred embodiments have likewise been described above. This group is preferably located in the ortho position relative to a heteroatom of A, in particular a nitrogen atom if one is present in A. A-$CR^{2B}R^{2B}H$ is preferably 2-methylfuran, 2,5-dimethylfuran, 2-ethylfuran, 1,2-dimethylpyrrole, 1,2,3-trimethylpyrrole, 1,3-dimethylpyrazole, 1,2-dimethylimidazole, 1-decyl-2-methylimidazole, 1-methyl-2-undecylimidazole, 2-picoline, 2-ethylpyridine, 2-propylpyridine, 2-benzylpyridine, 2,6-lutidine, 2,4-lutidine, 2,5-lutidine, 2,3-cycloheptenopyridine, 5-ethyl-2-methylpyridine, 2,4,6-collidine, 3-methylpyridazine, 4-methylpyrimidine, 4,6-dimethylpyrimidine, 2-methylpyrazine, 2-ethylpyrazine, 2,6-dimethylpyrazine, 2,5-dimethylpyrazine, 2,3-dimethylpyrazine, 2,3-diethylpyrazine, tetrahydroquinoxaline, tetramethylpyrazine, quinaldine, 2,4-dimethylquinoline, 2,6-dimethylquinoline, 2,7-dimethylquinoline, 2-methylquinoxaline, 2,3-dimethylquinxaline or neocuproin.

A-$CR^{2B}R^{2B}H$ is particularly preferably a group of the formula (IIIb)

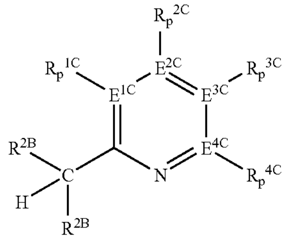

(IIIb)

where the variables have the following meanings:

$E^{1C}$-$E^{4C}$ are each carbon or nitrogen, $R^{1C}$-$R^{4C}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbons in the aryl part or $SiR^{5C}_3$, where the organic radicals $R^{1C}$-$R^{4C}$ may also be substituted by halogens or nitrogen or further $C_1$-$C_{20}$-alkyl groups, $C_2$-$C_{20}$-alkenyl groups, $C_6$-$C_{20}$-aryl groups, alkylaryl groups having from 1 to 10 carbon atoms in the alkyl part and 6-20 carbon atoms in the aryl part or $SiR^{5C}_3$ and two vicinal radicals $R^{1C}$-$R^{4C}$ or $R^{1C}$ and $R^{1B}$ may also be joined to form a five- or six-membered ring, $R^{5C}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{5C}$ may also be joined to form a five- or six-membered ring, p is 0 when $E^{1C}$-$E^{4C}$ is nitrogen and is 1 when $E^{1C}$-$E^{4C}$ is carbon and $R^{2B}$ are each, independently of one another, hydrogen, $C_1$-$C_{20}$-alkyl, $C_2$-$C_{20}$-alkenyl, $C_6C_{20}$-aryl, alkylaryl having from 1 to 10 carbon atoms in the alkyl part and 6-20 carbon atoms in the aryl part or $SiR^{3B}_3$, where the organic radicals $R^{2B}$ may also be substituted by halogens and $R^{2B}$ and A may also be joined to form a five- or six-membered ring, with one $R^{2B}$ preferably being as defined for $R^{1B}$.

In particular, 0 or 1 $E^{1C}$-$E^{4C}$ is nitrogen and the others are carbon. Particularly preferred A-$CR^{2B}R^{2B}H$ systems are 2-picoline, 2-ethylpyridine, 2-propylpyridine, 2-benzylpyridine, 2,6-lutidine, 2,4-lutidine, 2,5-lutidine, 2,3-cycloheptenopyridine, 5-ethyl-2-methylpyridine, 2,4,6-collidine, 3-methylpyridazine, 4-methylpyrimidine, 4,6-dimethylpyrimidine, 2-methylpyrazine, 2-ethylpyrazine, 2,6-dimethylpyrazine, 2,5-dimethylpyrazine, 2,3-dimethylpyrazine, 2,3-diethylpyrazine, tetrahydroquinoxaline, tetramethylpyrazine, quinaldine, 2,4-dimethylquinoline, 2,6-dimethylquinoline, 2,7-dimethylquinoline, 2-methylquinoxaline, 2,3-dimethylquinoxaline or neocuproin.

The A-$CR^{2B}R^{2B-}$ anion, in particular the A-$CR^{1B}R^{2B-}$ anion, formed after deprotonation can be isolated or preferably be reacted without further isolation with the cyclopentenone (IX). As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction with the cyclopentenone (IX) can be carried out at from −100 to +160° C., preferably from −80 to 100° C. and particularly preferably from 0 to 60° C. At temperatures above 40° C., preference is given to using aromatic or aliphatic solvents which contain no ether, or contain only a small proportion of ethers, as solvent.

The cyclopentenoxide formed by reaction of the A-$CR^{2B}R^{2B-}$ anion with the cyclopentenone (IX) is usually protonated prior to dehydration. This can, for example, be carried out by means of small amounts of acid, for example HCl, or by aqueous work-up. The intermediate obtained in this way, viz. a cyclopentenol, is subsequently dehydrated. This is often carried out with addition of catalytic amounts of acid such as HCl or p-toluenesulfonic acid or iodine. Dehydration can be carried out at from −10 to +160° C., preferably from 0 to 100° C. and particularly preferably from 20 to 80° C. As solvents, it is possible to use, for example, aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. Toluene and heptane are particularly useful. Water separators are often also used for dehydration.

This method of preparing the cyclopentadiene systems (VIIa) is particularly advantageous since it uses simple starting materials and gives good yields. The by-products formed (dehydration in the exo position) can also be separated off in a simple fashion by means of the further reactions to the monocyclopentadienyl complex. The cyclopentadiene system (VIIa) obtained in this way can then be deprotonated by customary methods, for example by means of potassium hydride or n-butyllithium, and reacted further with the appropriate transition metal compound, e.g. chromium trichloride tris(tetrahydrofuran), to give the corresponding monocyclopentadienyl complex (A). The by-products do not undergo any of these reactions. Furthermore, the cyclopentadienyl system (VIIa) can also be reacted directly with, for example, chromium amides to form the monocyclopentadienyl complex (A) using a method analogous to that described in EP-A-742 046.

The monocyclopentadienyl complexes of the present invention can be used alone or together with further components as catalyst systems for olefin polymerization. We have, furthermore, found catalyst systems for olefin polymerization which comprise A) at least one monocyclopentadienyl complex according to the present invention, B) optionally an organic or inorganic support, C) optionally one or more activating compounds, D) optionally one or more catalysts suitable for olefin polymerization and E) optionally one or more metal compounds containing a metal of group 1, 2 or 13 of the Periodic Table.

Thus, more than one of the monocyclopentadienyl complexes of the present invention can simultaneously be brought into contact with the olefin or olefins to be polymerized. This has the advantage that a wide range of polymers can be produced in this way. For example, bimodal products can be prepared in this fashion.

For the monocyclopentadienyl complexes of the present invention to be able to be used in polymerization processes in the gas phase or in suspension, it is often advantageous for the metallocenes to be used in the form of a solid, i.e. for them to be applied to a solid support B). Furthermore, the supported monocyclopentadienyl complexes have a high productivity. The monocyclopentadienyl complexes of the present invention can therefore optionally be immobilized on an organic or inorganic support B) and be used in supported form in the polymerization. This makes it possible, for example, to avoid deposits in the reactor and to control the polymer morphology. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polar functionalized polymers such as copolymers of ethene with acrylic esters, acrolein or vinyl acetate.

Particular preference is given to a catalyst system which comprises a monocyclopentadienyl complex according to the present invention and at least one activating compound C) and further comprises a support component B).

To obtain such a supported catalyst system, the unsupported catalyst system can be reacted with a support component B). The order in which the support component B), the monocyclopentadienyl complex A) according to the present invention and the activating compound C) are combined is in principle immaterial. The monocyclopentadienyl complex A) of the present invention and the activating compound C) can be immobilized independently of one another or simultaneously. After the individual process steps, the solid can be washed with suitable inert solvents such as aliphatic or aromatic hydrocarbons.

In a preferred variant of the preparation of the supported catalyst system, at least one of the monocyclopentadienyl complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monocyclopentadienyl complex catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277. A further preferred embodiment comprises firstly applying the activated component C) to the support component B) and subsequently bringing this supported compound into contact with the monocyclopentadienyl complex A) according to the present invention.

As support component B), preference is given to using finely divided supports which may be any organic or inorganic solid. In particular, the support component B) can be a porous support such as talc, a sheet silicate such as montmorillonite or mica, an inorganic oxide or a finely divided polymer powder (e.g. a polyolefin or a polar, functionalized polymer).

The support materials used preferably have a specific surface area in the range from 10 to 1 000 $m^2/g$, a pore volume in the range from 0.1 to 5 ml/g and a mean particle size of from 1 to 500 μm. Preference is given to supports having a specific surface area in the range from 50 to 700 $m^2/g$, a pore volume in the range from 0.4 to 3.5 ml/g and a mean particle size in the range from 5 to 350 μm. Particular preference is given to supports having a specific surface area in the range from 200 to 550 $m^2/g$, a pore volume in the range from 0.5 to 3.0 ml/g and a mean particle size of from 10 to 150 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1 000° C. in order to set, if appropriate, the desired structure of the solid and/or the desired OH concentration on the surface. The support can also be treated chemically using customary desiccants such as metal alkyls, preferably aluminum alkyls, chlorosilanes or $SiCl_4$, or else methylalumoxane. Appropriate treatment methods are described, for example, in WO 00/31090.

The inorganic support material can also be chemically modified. For example, treatment of silica gel with $NH_4SiF_6$ or other fluorinating agents leads to fluorination of the silica gel surface, while treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and should preferably likewise be freed of adhering moisture, solvent residues or other impurities by means of appropriate purification and drying operations before use. It is also possible to use functionalized polymer supports, e.g. functionalized supports based on polystyrene, polyethylene or polypropylene, by whose functional groups; for example ammonium or hydroxy groups, at least one of the catalyst components can be immobilized.

Suitable inorganic oxides as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Further inorganic oxides which can be used alone or in combination with the abovementioned preferred oxidic supports are, for example, MgO, CaO, $AlPO_4$, $ZrO_2$, $TiO_2$, $B_2O_3$ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. The silica gels can be dried and/or calcined before use.

Further preferred supports B) are hydrotalcites and calcined hydrotalcites. In mineralogy, hydrotalcite is a natural mineral having the ideal formula $$Mg_6Al_2(OH)_{16}CO_3.4\ H_2O$$

whose structure is derived from that of brucite $Mg(OH)_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula $$M(II)_{2x}{}^{2+}M(III)_2{}^{3+}(OH)_{4x+4}.A_{2/n}{}^{n-}.z\ H_2O$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or $B(OH)_4^-$ or polyoxo metal anions such as $Mo_7O_{24}^{6-}$ or $V_{10}O_{28}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1 000° C., in particular from 400° C. to 700° C. It is possible for air or inert gas to be passed over the solid during calcination or for a vacuum to be applied.

On heating, the natural or synthetic hydrotalcites firstly give off water, i.e. drying occurs. On further heating, the actual calcination, the metal hydroxides are converted into the metal oxides by elimination of hydroxyl groups and interstitial anions; OH groups or interstitial anions such as carbonates can also still be present in the calcined hydrotalcites. A measure of this is the loss on ignition. This is the weight loss experienced by a sample which is heated in two steps, firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter $d_{50}$ of from 5 to 200 μm, preferably from 10 to 150 μm, particularly preferably from 15 to 100 μm and in particular from 20 to 70 μm, and usually have pore volumes of from 0.1 to 10 $cm^3/g$, preferably from 0.2 to 5 $cm^3/g$, and specific surface areas of from 30 to 1 000 $m^2/g$, preferably from 50 to 800 $m^2/g$ and in particular from 100 to 600 $m^2/g$. The monocyclopentadienyl complexes of the present invention are preferably applied in such an amount that the concentration of monocyclopentadienyl complexes in the finished catalyst system is from 5 to 200 μmol, preferably from 20 to 100 μmol and particularly preferably from 25 to 70 μmol, per g of support B).

Some of the monocyclopentadienyl complexes of the present invention have little polymerization activity on their own and are then brought into contact with an activator, viz. the component C), to be able to display good polymerization activity. For this reason, the catalyst system optionally further comprises, as component C), one or more activating compounds, preferably at least one cation-forming compound C).

Suitable compounds C) which are able to react with the monocyclopentadienyl complex A) to convert it into a catalytically active, or more active, compound are, for example, compounds such as an aluminoxane, a strong uncharged Lewis acid, an ionic compound having a Lewis acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formula (X) or (XI)

(X)

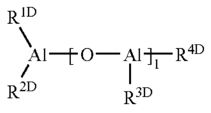

(XI)

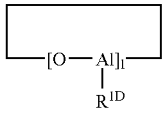

where $R^{1D-R4D}$ are each, independently of one another, a $C_1$-$C_6$-alkyl group, preferably a methyl, ethyl, butyl or isobutyl group, and I is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that I is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the monocyclopentadienyl complexes A) and the aluminoxane compounds in such amounts that the atomic ratio of aluminum from the aluminoxane compounds including any aluminum alkyl still present to the transition metal from the monocyclopentadienyl complex A) is in the range from 1:1 to 1 000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monocyclopentadienyl complex A) is usually in the range from 1:1 to 100:1, preferably from 10:1 to 50:1 and in particular in the range from 20:1 to 40:1. Preference is given to using a monocyclopentadienyl metal dialkyl compound A).

As strong, uncharged Lewis acids, preference is given to compounds of the formula (XII)

$$M^{2D}X^{1D}X^{2D}X^{3D} \quad (XII)$$

where $M^{2D}$ is an element of group 13 of the Periodic Table of the Elements, in particular B, Al or Ga, preferably B, $X^{1D}$, $X^{2D}$ and $X^{3D}$ are each hydrogen, $C_1$-$C_{10}$-alkyl, $C_6$-$C_{15}$-aryl, alkylaryl, arylalkyl haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which $X^{1D}$, $X^{2D}$ and $X^{3D}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2,2',3,3',4,4',5,5',6,6'-nonafluorobiphenyl, triethylaluminum/pentafluorophenol and triisobutylaluminum/pentafluorophenol and triethylaluminum/4,4'-dihydroxy-2,2',3,3',5,5',6,6'-octafluorobiphenyl hydrate.

In further suitable aluminum and boron compounds of the formula (XII), $R^{1D}$ is an OH group. Examples of compounds of this type are boronic acids and borinic acids, in particular borinic acids having perfluorinated-aryl radicals, for example $(C_6F_5)_2BOH$.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

Suitable ionic compounds having Lewis-acid cations include salt-like compounds of the cation of the formula (XIII)

$$[((M^{3D})^{a+})Q_1Q_2 \ldots Q_z]^{d+} \quad (XIII)$$

where $M^{3D}$ is an element of groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, d corresponds to the difference a-z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 97/36937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or a borate anion to be joined to a borane, as in the dianion $[(C_6F_5)_2B—C_6F_4—B(C_6F_5)_3]^{2-}$, the anion $[(C_6F_5)_3B—CN—B(C_6F_5)_3]^{2-}$, or the borate anion can be bound to the support surface via a bridge bearing a suitable functional group.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents, based on the monocyclopentadienyl complex A).

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the monocyclopentadienyl complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

A likewise broad product spectrum can be achieved by use of the monocyclopentadienyl complexes A) of the present invention in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups 3 to 12 of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl groups and ligands which are free of cyclopentadienyl groups. A large number of such compounds D) suitable for olefin polymerization are described in Chem. Rev. 2000, vol, 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene complexes. Particularly useful metallocene complexes are those of the formula (XIV)

(XIV)

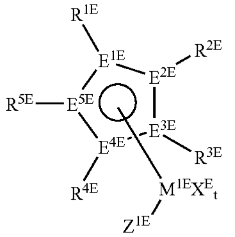

where the substituents and indices have the following meanings:

$M^{1E}$ is titanium, zirconium, hafnium, vanadium, niobium, tantalum, chromium, molybdenum or tungsten, or an element of group 3 of the Periodic Table and the lanthanides, $X^E$ is fluorine, chlorine, bromine, iodine, hydrogen, $C_1$-$C_{10}$-alkyl, $C_2$-$C_{10}$-alkenyl, $C_6$-$C_{15}$-aryl, alkylaryl having from 1 to 10 carbon atoms in the alkyl part and from 6 to 20 carbon atoms in the aryl part, —$OR^{6E}$ or —$NR^{6E}R^{7E}$, or two radicals $X^E$ form a substituted or unsubstituted diene ligand, in particular a 1,3-diene ligand, and the radicals $X^E$ are identical or different and may be joined to one another, $E^{1E}$-$E^{5E}$ are each carbon or not more than one $E^{1E}$ to $E^{5E}$ is phosphorus or nitrogen, preferably carbon, t is 1, 2 or 3 and is such that, depending on the valence of $M^{1E}$, the metallocene complex of the formula (XIV) is uncharged, where $R^{6E}$ and $R^{7E}$ are each $C_1$-$C_{10}$-alkyl, $C_6$-$C_{15}$-aryl, alkylaryl, arylalkyl, fluoroalkyl or fluoroaryl, each having from 1 to 10 carbon atoms in the alkyl radical and from 6 to 20 carbon atoms in the aryl radical, and $R^{1E}$ to $R^{5E}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{8E}_2$, $N(SiR^{8E}_3)_2$, $OR^{8E}$, $OSiR^{8E}_3$, $SiR^{8E}_3$, where the organic radicals $R^{1E}$-$R^{5E}$ may also be substituted by halogens and/or two radicals $R^{1E}$-$R^{5E}$, in particular vicinal radicals, may also be joined to form a five-, six- or seven-membered ring, and/or two vicinal radicals $R^{1E}$-$R^{5E}$ may be joined to form a five-, six- or seven-membered heterocycle which contains at least one atom from the group consisting of N, P, O and S, where $R^{8E}$ can be identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy and $Z^{1E}$ is as defined for $X^E$ or is

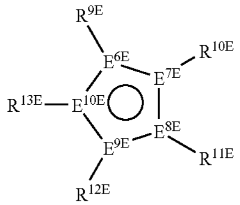

where the radicals $R^{9E}$ to $R^{13E}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{14E}_2$, $N(SiR^{14E}_3)_2$, $OR^{14E}$, $OSiR^{14E}_3$, $SiR^{14E}_3$, where the organic radicals $R^{9E}$-$R^{13E}$ may also be substituted by halogens and/or two radicals $R^{9E}$-$R^{13E}$, in particular vicinal radicals, may also be joined to form a five-, six- or seven-membered ring, and/or two vicinal radicals $R^{9E}$-$R^{13E}$ may be joined to form a five-, six- or seven-membered heterocycle which contains at least one atom from the group consisting of N, P, O and S, where $R^{14E}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6E}$-$E^{10E}$ are each carbon or not more than one $E^{6E}$ to $E^{10E}$ is phosphorus or nitrogen, preferably carbon, or the radicals $R^{4E}$ and $Z^{1E}$ together form an —$R^{15E}_v$-$A^{1E}$- group in which $R^{15E}$ is

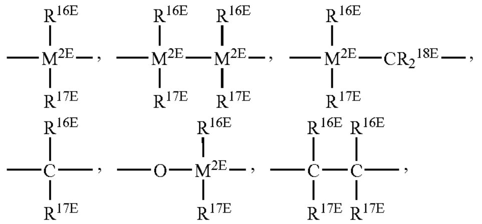

-continued

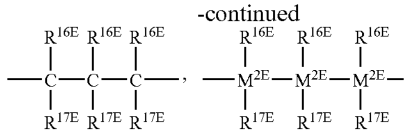

$=BR^{16E}$, $=BNR^{16E}R^{17E}$, $=AlR^{16E}$, —Ge—, —Sn—, —O—, —S—, $=SO$, $=SO_2$, $=NR^{16E}$, $=CO$, $=PR^{16E}$ or $=P(O)R^{16E}$, where $R^{16E}$, $R^{17E}$ and $R^{18E}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms, and $M^{2E}$ is silicon, germanium or tin, preferably silicon, $A^{1E}$ is

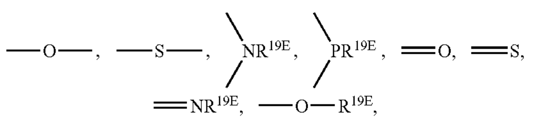

$—NR^{19E}_2$, $—PR^{19E}_2$ or an unsubstituted, substituted or fused, heterocyclic ring system, where $R^{19E}$ are each, independently of one another, $C_1$-$C_{10}$-alkyl, $C_6$-$C_{15}$-aryl, $C_3$-$C_{10}$-cycloalkyl, $C_7$-$C_{18}$-alkylaryl or $Si(R^{20E})_3$, $R^{20E}$ is hydrogen, $C_1$-$C_{10}$-alkyl, $C_6$-$C_{15}$-aryl which may in turn bear $C_1$-$C_4$-alkyl groups as substituents or $C_3$-$C_{10}$-cycloalkyl, v is 1 or when $A^{1E}$ is an unsubstituted, substituted or fused, heterocyclic ring system may also be 0, or the radicals $R^{4E}$ and $R^{12E}$ together form an $—R^{15E}$-group.

$A^{1E}$ together with the bridge $R^{15E}$ can, for example, form an amine, ether, thioether or phosphine. However, $A^{1E}$ may also be an unsubstituted, substituted or fused, heterocyclic aromatic ring system which can contain heteroatoms from the group consisting of oxygen, sulfur, nitrogen and phosphorus in addition to carbon atoms in the ring. Examples of five-membered heteroaryl groups which can contain from one to four nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which can contain from one to four nitrogen atoms and/or a phosphorus atom, are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

It is preferred that the radicals $X^E$ in the formula (XIV) are identical, preferably fluorine, chorine, bromine, $C_1$-$C_7$-alkyl or aralkyl, in particular chlorine, methyl or benzyl.

The synthesis of such complexes can be carried out by methods known per se, preferably by reaction of the appropriately substituted, cyclic hydrocarbon anions with halides of titanium, zirconium, hafnium or chromium.

Among the metallocene complexes of the formula (XIV), preference is given to (XIV a)

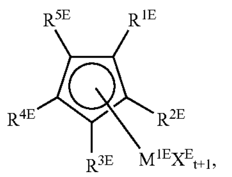

(XIVb)

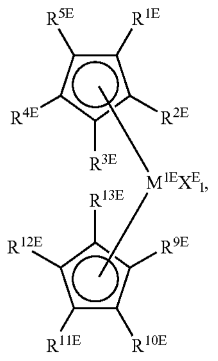

(XIVc)

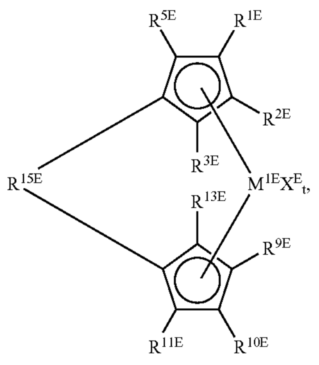

-continued (XIVd)

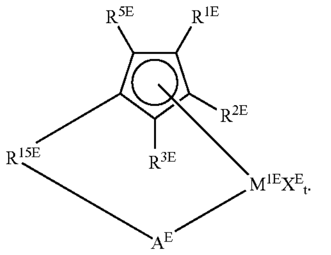

Among the compounds of the formula (XIVa), particular preference is given to those in which $M^{1E}$ is titanium, vanadium or chromium, $X^E$ is chlorine, $C_1$-$C_4$-alkyl, phenyl, alkoxy or aryloxy, t is 1 or 2 and $R^{1E}$ to $R^{5E}$ are each hydrogen or $C_1$-$C_6$-alkyl or two adjacent radicals $R^{1E}$ to $R^{5E}$ form a substituted or unsubstituted benzo group.

Among the compounds of the formula (XIVb), preference is given to those in which $M^{1E}$ is titanium, zirconium, vanadium, hafnium or chromium, $X^E$ is fluorine, chlorine, $C_1$-$C_4$-alkyl or benzyl, or two radicals $X^E$ form a substituted or unsubstituted butadiene ligand, t is 0 in the case of chromium, otherwise 1 or 2, preferably 2, $R^{1E}$ to $R^{5E}$ are each hydrogen, $C_1$-$C_8$-alkyl, $C_6$-$C_8$-aryl, $NR^{8E}_2$, $OSiR^{8E}_3$ or $Si(R^{8E})_3$ and $R^{9E}$ to $R^{13E}$ are each hydrogen, $C_1$-$C_8$-alkyl or $C_6$-$C_8$-aryl, $NR^{14E}_2$, $OSiR^{14E}_3$ or $Si(R^{14E})_3$ or two radicals $R^{1E}$ to $R^{5E}$ and/or $R^{9E}$ to $R^{13E}$ together with the $C_5$ ring form an indenyl or substituted indenyl system.

The compounds of the formula (XIVb) in which the cyclopentadienyl radicals are identical are particularly useful.

Examples of particularly useful compounds D) of the formula (XIVb) include: bis(cyclopentadienyl)zirconium dichloride, bis(pentamethylcyclopentadienyl)zirconium dichloride, bis(methylcyclopentadienyl)zirconium dichloride, bis(ethylcyclopentadienyl)zirconium dichloride, bis(n-butylcyclopentadienyl)zirconium dichloride, bis(1-n-butyl-3-methylcyclopentadienyl)-zirconium dichloride, bis(indenyl)zirconium dichloride, bis(tetrahydroindenyl)zirconium dichloride and bis(trimethylsilylcyclopentadienyl)zirconium dichloride and also the corresponding dimethylzirconium compounds.

Particularly useful compounds of the formula (XIVc) are those in which $R^{15E}$ is

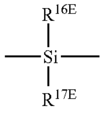 or 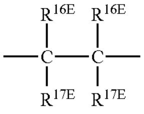

or $=BR^{16E}$ or $=BNR^{16E}R^{17E}$, $M^{1E}$ is titanium, zirconium or hafnium, in particular zirconium, and $X^E$ are identical or different and are each chlorine, $C_1$-$C_4$-alkyl, benzyl, phenyl or $C_7$-$C_{15}$-alkylaryloxy.

Particularly useful compounds of the formula (XIVc) are those of the formula (XIVc')

(XIVc')

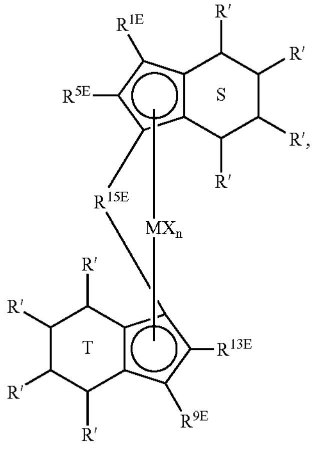

where the radicals R' are identical or different and are each-hydrogen, $C_1$-$C_{10}$-alkyl or $C_3$-$C_{10}$-cycloalkyl, preferably methyl, ethyl, isopropyl or cyclohexyl, $C_6$-$C_{20}$-aryl, preferably phenyl, naphthyl or mesityl, $C_7$-$C_{40}$-arylalkyl, $C_7$-$C_{40}$-alkylaryl, preferably 4-tert-butylphenyl or 3,5-di-tert-butylphenyl, or $C_8$-$C_{40}$-arylalkenyl, $R^{5E}$ and $R^{13E}$ are identical or different and are each hydrogen, $C_1$-$C_6$-alkyl, preferably methyl, ethyl, isopropyl, n-propyl, n-butyl, n-hexyl or tert-butyl, and the rings S and T may be identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6, positions, the 2,4,6 positions, the 2,5,6 positions, the 2,4,5,6 positions or the 2,4,5,6,7 positions, in particular in the 2,4 positions, with the following numbering applying to the site of substitution:

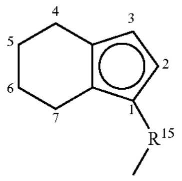

Furthermore, preference is given to using bridged bis-indenyl complexes in the rac or pseudo-rac form as component D). The term “pseudo-rac form” refers to complexes in which the two indenyl ligands are in the rac arrangement relative to one another when all other substituents of the complex are disregarded.

Further examples of particularly useful catalysts D) (XIVc) and (XIVc') include: dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluorenylcyclopentadienylzirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(2-methylindenylyzirconium dichloride, dimethylsilanediylbis(2-isopropylindenyl)zirconium dichloride, dimethylsilanediylbis(2-tert-butylindenyl)zirconium dichloride, diethylsilanediylbis(2-methylindenyl)zirconium dibromide, dimethylsilanediylbis(3-methyl-5-methylcyclopentadienyl)zirconium dichloride, dimethylsilanediylbis(3-ethyl-5-isopropylcyclopentadienyl) zirconium dichloride, dimethylsilanediylbis(2-ethylindenyl) zirconium dichloride, dimethylsilanediylbis(2-methyl-4,5-benzindenyl)zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis (2-methyl-4-(1-naphthyl)indenyl)zirconium dichloride, dimethylsilanediylbis(2-ethyl-4-(1-naphthyl)indenyl)zirconium dichloride, dimethylsilanediylbis (2-propyl-4-(1-naphthyl)indenyl)zirconium dichloride, dimethylsilanediylbis(2-i-butyl-4-(1-naphthyl)indenyl)zirconium dichloride, dimethylsilanediylbis(2-propyl-4-(9-phenanthryl)indenyl) zirconium dichloride, dimethylsilanediylbis(2-methyl-4-isopropylindenyl)zirconium dichloride, dimethylsilanediylbis (2,7-dimethyl-4-isopropylindenyl)zirconium dichloride, dimethylsilanediylbis (2-methyl-4,6-diisopropylindenyl)zirconium dichloride, dimethylsilanediylbis(2-methyl-4[p-trifluoromethylphenyl]indenyl)zirconium dichloride, dimethylsilanediylbis(2-methyl-4-[3',5'-dimethylphenyl]indenyl) zirconium dichloride, dimethylsilanediylbis(2-methyl-4-[4'-tert-butylphenyl]indenyl)zirconium dichloride, diethylsilanediylbis(2-methyl-4-[4'-tert-butylphenyl]indenyl)zirconium dichloride, dimethylsilanediylbis(2-ethyl-4-[4'-tert-butylphenyl]indenyl)zirconium dichloride, dimethylsilanediylbis(2-propyl-4-[4'-tert-butylphenyl]indenyl) zirconium dichloride, dimethylsilanediylbis(2-isopropyl-4-[4'-tert-butylphenyl]indenyl)zirconium dichloride, dimethylsilanediylbis(2-n-butyl-4-[4'-tert-butylphenyl]indenyl)zirconium dichloride, dimethylsilanediylbis(2-hexyl-4-[4'-tert-butylphenyl]indenyl)zirconium dichloride, dimethylsilanediyl-(2-isopropyl-4-phenylindenyl)(2-methyl-4-phenylindenyl)zirconium dichloride, dimethylsilanediyl(2-isopropyl-4-(1-naphthyl)indenyl)(2-methyl-4-(1-naphthyl) indenyl)zirconium dichloride, dimethylsilanediyl(2-isopropyl)-4-[4'-tert-butylphenyl]indenyl)(2-methyl-4-[4'-tert-butylphenyl]indenyl)zirconium dichloride, dimethylsilanediyl(2-isopropyl-4-[4'-tert-butylphenyl]-indenyl)(2-ethyl-4-[4'-tert-butylphenyl]indenyl)zirconium dichloride, dimethylsilanediyl(2-isopropyl-4-[4'-tert-butylphenyl]indenyl)(2-methyl-4-[3',5'-bis-tert-butylphenyl] indenylzirconium dichloride, dimethylsilanediyl(2-isopropyl-4-[4'-tert-butylphenyl]indenyl)(2-methyl-4-[1'-naphthyl]indenyl)zirconium dichloride and ethylene(2-isopropyl-4-[4'-tert-butylphenyl]indenyl)(2-methyl-4-[4'-tertbutylphenyl]indenyl)zirconium dichloride, and also the corresponding dimethylzirconium, zirconium monochloride mono(alkylaryloxide) and zirconium di(alkylaryloxide) compounds. The complexes are preferably used in the rac form.

Such complexes can be synthesized by methods known per se, preferably by reaction of the appropriately substituted, cyclic hydrocarbon anions with halides of titanium, zirconium, hafnium, vanadium, niobium, tantalum or chromium. Examples of appropriate preparative methods are described, inter alia, in Journal of Organometallic Chemistry, 369 (1989), 359-370.

Particularly useful compounds of the formula (XIVd) are those in which $M^{1E}$ is titanium or zirconium, in particular titanium, and $X^E$ is chlorine, $C_1$-$C_4$-alkyl or phenyl or two radicals X form a substituted or unsubstituted butadiene ligand, $R^{15E}$ is

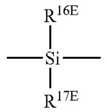
or
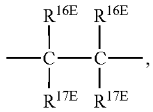
, or $=BR^{16E}$ or $=BNR^{16E}R^{17E}$, $A^{1E}$ is

—O—, —S— or
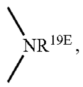
, t is 1 or 2, preferably 2, $R^{1E}$ to $R^{3E}$ and $R^{5E}$ are each hydrogen, $C_1$-$C_{10}$-alkyl, preferably methyl, $C_3$-$C_{10}$-cycloalkyl, $C_6$-$C_{15}$-aryl, $NR^{8E}_2$ or $Si(R^8)_3$, or two adjacent radicals form a cyclic group having from 4 to 12 carbon atoms, with particular preference being given to all $R^{1E}$ to $R^{3E}$ and $R^{5E}$ being methyl.

Particularly useful complexes D) of the formula (XIVd) are dimethylsilanediyl(tetramethylcyclopentadienyl)(benzylamino)titanium dichloride, dimethylsilanediyl(tetramethylcyclopentadienyl)(tertbutylamino)titanium dichloride, dimethylsilanediyl(tetramethylcyclopentadienyl)(adamantyl) titanium dichloride and dimethylsilanediyl(indenyl)(tert-butylamino)titanium dichloride.

Another group of compounds of the formula (XIVd) which are particularly useful are those in which $M^{1E}$ is titanium, vanadium or chromium, preferably in the oxidation state III, and $X^E$ is chlorine, $C_1$-$C_4$-alkyl or phenyl or two radicals $X^E$ form a substituted or unsubstituted butadiene ligand, $R^{15E}$ is

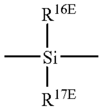
or
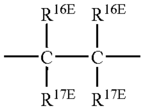
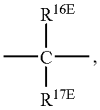
,
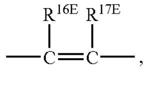
,

, or $=BR^{16E}$ or $=BNR^{18E}R^{17E}$, $A^{1E}$ is —O—$R^{19E}$,—$NR^{19E}_2$,—$PR^{19E}_2$ or an unsubstituted, substituted or fused, heterocyclic, in particular heteroaromatic, ring system, v is 1 or when $A^{1E}$ is an unsubstituted, substituted or fused, heterocyclic ring system may be 0 or 1, $R^{1E}$ to $R^{3E}$ and $R^{5E}$ are each hydrogen, $C_1$-$C_{10}$-alkyl, $C_3$-$C_{10}$-cycloalkyl, $C_6$-$C_{15}$-aryl or $Si(R^{8E})_3$, or two adjacent radicals form a cyclic group having from 4 to 12 carbon atoms.

In a preferred embodiment, $A^{1E}$ is an unsubstituted, substituted or fused, heteroaromatic ring system and $M^{1E}$ is chromium. Very particular preference is given to $A^{1E}$ being an unsubstituted or substituted, e.g. alkyl-substituted quinolyl or pyridyl bound in position 8 or 2, e.g. 8-quinolyl, 8-(2-methylquinolyl), 8-(2,3,4-trimethylquinolyl), 8-(2,3,4,5,6,7-hexamethylquinolyl), v being 0 and $M^{1E}$ being chromium. Preferred catalysts D) of this type are 1-(8-quinolyl)-2-methyl-4-methylcyclopentadienylchromium(III)dichloride, 1-(8-quinolyl)-3-isopropyl-5-methylcyclopentadienylchromium (III)dichloride, 1-(8-quinolyl)-3-tert-butyl-5-methylcyclopentadienylchromium(III)dichloride, 1-(8-quinolyl)-2,3,4,5-tetramethylcyclopentadienylchromium (III)dichloride, 1-(8-quinolyl)tetrahydroindenylchromium (III)dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl)benzindenylchromium(III) dichloride, 1-(8-quinolyl)-2-methylbenzindenyl-chromium (III)dichloride, 1-(8-(2-methylquinolyl))-2-methyl-4-methylcyclopentadienylchromium(III)dichloride, 1-(8-(2-methylquinolyl)-2,3,4,5-tetramethylcyclopentadienylchromium(III)dichloride, 1-(8-(2-methylquinolyl))tetrahydroindenylchromium(III) dichloride, 1-(8-(2-methylquinolyl))indenylchromium(III) dichloride, 1-(8-(2-methylquinolyl))-2-methylindenylchromium(III)dichloride, 1-(8-(2-methylquinolyl))-2-isopropylindenylchromium(III) dichloride, 1-(8-(2-methylquinolyl))-2-ethylindenylchromium(III)dichloride, 1-(8-(2-methylquinolyl))-2-tert-butylindenylchromium(III) dichloride, 1-(8-(2-methylquinolyl))benzindenylchromium (III)dichloride or 1-(8-(2-methylquinolyl))-2-methylbenzindenylchromium(III)dichloride.

Furthermore, owing to the ease of preparation, preference is given to compounds in which $R^{15E}$ is CH═CH or 1,2-phenylene and $A^{1E}$ is $NR^{19E}_2$, and compounds in which $R^{15E}$ is $CH_2$, $C(CH_3)_2$ or $Si(CH_3)_2$ and $A^{1E}$ is unsubstituted or substituted 8-quinolyl or unsubstituted or substituted 2-pyridyl.

The preparation of such functional cyclopentadienyl ligands has been known for a long time. Various synthetic routes to these complexing ligands are described, for example, by M. Enders et al. in Chem. Ber. (1996), 129, 459-463, or P. Jutzi and U. Siemeling in J. Orgmet Chem. (1995), 500, 175-185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed from a cyclopentadienyl or heterocyclopentadienyl and a fused-on heterocycle, with the heterocycles preferably being aromatic and containing nitrogen and/or sulfur. Such compounds are described, for example, in WO 98/22486. These are in particular dimethylsilanediyl(2-methyl-4-phenylindenyl)(2,5-dimethyl-N-phenyl-4-azapentalene)zirconium dichloride, dimethylsilanediylbis(2-methyl-4-phenyl-4-hydroazulenyl)zirconium dichloride, dimethylsilanediylbis(2-ethyl-4-phenyl-4-hydroazulenyl)zirconium dichloride, bis(2,5-dimethyl-N-phenyl-4-azapentalene)zirconium dichloride or (indenyl)(2,5-dimethyl-N-phenyl-4-azapentalene)zirconium dichloride.

Further suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5-tri(methyl)-1,3,5-triazacyclohexane]-chromium trichloride, [1,3,5-tri(ethyl)-1,3,5-triazacyclohexane]chromium trichloride, [1,3,5-tri(octyl)-1,3,5-triazacyclohexane]chromium trichloride, [1,3,5-tri (dodecyl)-1,3,5-triazacyclohexane]chromium trichloride and [1,3,5-tri(benzyl)-1,3,5-triazacyclohexane]chromium trichloride.

Further suitable catalysts D) are, for example, transition metal complexes with at least one ligand of the formulae XV to XIX,

XV

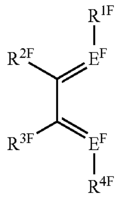

XVI

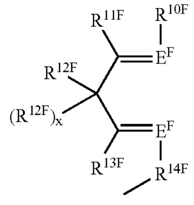

XVII

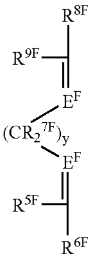

XVIII

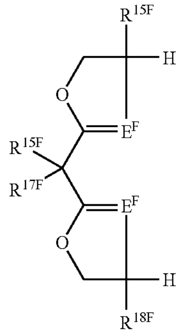

-continued

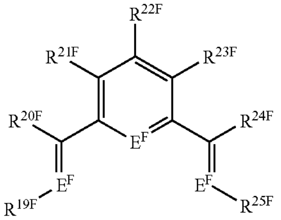

XIX where the transition metal is selected from among the elements Ti, Zr, Hf, Sc, V, Nb, Ta, Cr, Mo, W, Fe, Co, Ni, Pd, Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three $E^F$ in a molecule can be identical or different.

The radicals $R^{1F}$ to $R^{25F}$, which may be identical or different within a ligand system XV to XIX, are as follows:

$R^{1F}$ and $R^{4F}$ are each, independently of one another, hydrocarbon radicals or substituted hydrocarbon radicals, preferably hydrocarbon radicals in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{3F}$ together may also form a ring system in which one or more heteroatoms may be present, $R^{6F}$ and $R^{8F}$ are each, independently of one another, hydrocarbon radicals or substituted hydrocarbon radicals, $R^{5F}$ and $R^{9F}$ are each, independently of one another, hydrogen, a hydrocarbon radical or a substituted hydrocarbon radical, where $R^{6F}$ and $R^{5F}$ or $R^{3F}$ and $R^{9F}$ may together also form a ring system, $R^{7F}$ are each, independently of one another, hydrogen, a hydrocarbon radical or a substituted hydrocarbon radical, where two $R^{7F}$ may together also form a ring system, $R^{10F}$ and $R^{14F}$ are each, independently of one another, hydrocarbon radicals or substituted hydrocarbon radicals, $R^{11F}$, $R^{12F}$, $R^{12F'}$ and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may together form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$-$C_{20}$-alkenyl, $C_6$-$C_{20}$-aryl, alkylaryl having from 1 to 10 carbon atoms in the alkyl part and 6-20 carbon atoms in the aryl part, where the organic radicals $R^{16F}$ and $R^{25F}$ may also be substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the, alkyl part and 6-20 carbon atoms in the aryl part or $SiR^{26F}_3$, where the organic radicals $R^{20F}$-$R^{24F}$ may also be substituted by halogens and two vicinal radicals $R^{20F}$-$R^{24F}$ may also be joined to form a five- or six-membered ring and $R^{26F}$ are each, independently of one another, hydrogen, $C_1$-$C_{20}$-alkyl; $C_2$-$C_{20}$-alkenyl, $C_5$-$C_{20}$-aryl or alkylaryl having from 1 to 10 carbon atoms in the alkyl part and 6-20 carbon atoms in the aryl part and two radicals $R^{26F}$ may also be joined to form a five- or six-membered ring.

x is 0 or 1, with the complex of the formula (XVI) being negatively charged when x=0, and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.:

di(2,6-di-i-propylphenyl)-2,3-dimethyldiazabutadienepalladium dichloride, di(di-i-propylphenyl)-2,3-dimethyldiazabutadienenickel dichloride, di(2,6-di-i-propylphenyl) dimethyldiazabutadienedimethylpalladium, di(2,6-di-i-propylphenyl)-2,3-dimethyldiazabutadienedimethylnickel, di(2,6-dimethylphenyl)-2,3-dimethyldiazabutadienepalladium dichloride, di(2,5-dimethylphenyl)-2,3-dimethyldiazabutadienenickel dichloride, di(2,6-dimethylphenyl)-2,3-dimethyldiazabutadienedimethylpalladium, di(2,6-dimethylphenyl)-2,3-dimethydiazabutadienedimethynickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'-bipyridylpalladium dichloride, 1,1'-bipyridylnickel dichloride, 1,1'-bipyridyl(dimethyl)palladium, 1,1'-bipyridyl(dimethyl)nickel.

Particularly useful compounds (XIX) also include those which are described in J. Am. Chem. Soc. 120, p. 4049 ff. (1998), J. Chem. Soc., Commun. 1998, 849, and WO 98/27124. $E^F$ is preferably nitrogen and $R^{19F}$ and $R^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl and 2,4,6-trimethylphenyl. At the same time, $R^F$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands XIX with the transition metals Fe, Co or Ni, in particular Fe. Particular preference is given to 2,6-diacetylpyridinebis(2,4-dimethylphenylimine) iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis-(2,6-dichlorophenylimine)iron dichloride, 2,6-pyridinedicarboxaldehydebis(2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride, and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with pi ligands having one or more heteroatoms in the pi system, for example the boratabenzene ligand, the pyrrolyl anion or the phospholyl anion, can also be used as catalysts D).

Further complexes suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one monocyclopentadienyl complex A) in the presence of at least one catalyst D) customary for the polymerization of olefins and if desired, one or more activating compounds C). Here, depending on the catalyst combinations A) and D), one more activating compounds C) may be advantageous. The polymerization catalysts D) can likewise be supported and can be used simultaneously or in any order with the complex A) of the present invention. For example, the monocyclopentadienyl complex A) and the polymerization catalysts D) can be applied together to a support B) or different supports B). It is also possible to use mixtures of various catalysts as component D). The molar ratio of monocyclopentadienyl complex A) to polymerization catalyst D) is usually in the range from 1:100 to 100:1, preferably from 1:10 to 20:1 and particularly preferably from 1:1 to 10:1.

The catalyst system may further comprise, as additional component E), a metal compound of the formula (XX), $$M^G(R^{1G})_{r^G}(R^{2G})_{s^G}(R^{3G})_{t^G} \quad (XX)$$

where $M^G$ is Li, Na, K, Be, Mg, Ca, Sr, Ba, boron, aluminum, gallium, indium, thallium, zinc, in particular Li, Na, K, Mg, boron, aluminum or Zn, $R^{1G}$ is hydrogen, $C_1$-$C_{10}$-alkyl, $C_5$-$C_{15}$-aryl, alkylaryl or arylalkyl each having from 1 to 10 carbon atoms in the alkyl part and from 6 to 20 carbon atoms in the aryl part, $R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl radical and from 6 to 20 carbon atoms in the aryl radical, or alkoxy with $C_1$-$C_{10}$-alkyl or $C_6$-$C_{15}$-aryl, $r^G$ is an integer from 1 to 3 and $s^G$ and $t^G$ are integers from 0 to 2, with the sum $r^G+s^G+t^G$ corresponding to the valence of $M^G$, where the component E) is not identical to the component C). It is also possible to use mixtures of various metal compounds of the formula (XX).

Among the metal compounds of the formula (XX), preference is given to those in which $M^G$ is lithium, magnesium, boron or aluminum and $R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethyl-aluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from monocyclopentadienyl compound A) is from 2 000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of a chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment the monocyclopentadienyl complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the cation-forming compound C) to the support B) and subsequently bringing this supported cation-forming compound into contact with the monocyclopentadienyl complex A).

The component D) can likewise be reacted in any order with the components A) and, if desired, B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the α-olefin to be polymerized and the catalyst solid comprising the components A), B) and C) as described above subsequently being added.

The monocyclopentadienyl complex A) can be brought into contact with the component(s) C) and/or D) either before or after being brought into contact with the olefins to be polymerized. Preactivation using one or more components C) prior to mixing with the olefin and further addition of the same or different components C) and/or D) after the mixture has been brought into contact with the olefin is also possible. Preactivation is generally carried out at 10-100° C., preferably 20-80° C.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:1 000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1 000 to 1 000:1, preferably from 1:5 to 20:1.

The catalyst systems of the present invention are suitable for the polymerization of olefins and especially for the polymerization of α-olefins, i.e. hydrocarbons having terminal double bonds. Suitable monomers include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to nonpolar olefinic compounds, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated and unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene and methylnorbornene and dienes such as 5-ethylidene-2-norbornene, norbornadiene or ethylnorbornadiene.

Mixtures of two or more olefins can also be polymerized. In contrast to some known iron and cobalt complexes, the monocyclopentadienyl complexes of the present invention display a good polymerization activity even in the case of higher α-olefins, so that their suitability for copolymerization deserves particular emphasis. In particular, the monocyclopentadienyl complexes of the present invention can be used for the polymerization or copolymerization of ethene or propene. As comonomers in the polymerization of ethene, preference is given to using $C_3$-$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually cared out at from −60 to 350° C. under pressures of from 0.5 to 4 000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1 000 to 4 000 bar, in particular from 2 000 to 3 500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. Nos. 3,242,150 and 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The monocyclopentadienyl complexes of the present invention and the catalyst systems in which they are present can also be prepared by means of combinatorial chemistry methods or their polymerization activity can be tested with the aid of these combinatorial methods.

The process of the present invention allows polymers of olefins to be prepared. The term "polymerization" as used here in the description of the present invention encompasses both polymerization and oligomerization, i.e. oligomers and polymers having molar masses $M_w$ in the range from about 56 to 10 000 000 can be produced by this process.

Owing to their good mechanical properties, the olefin polymers prepared using the catalyst system of the present invention are particularly useful for the production of films, fibers and moldings.

The catalyst systems of the present invention give a very high productivity in the polymerization of olefins, offer advantages in the work-up of the polymers after the polymerization and lead to significantly fewer problems in respect of catalyst residues in the polymer. The polymers prepared using the catalyst system of the present invention are particularly useful for applications which require a high productivity. In addition, the catalyst systems of the present invention display a very good activity even at a relatively low molar ratio of aluminoxane to transition metal compound.

EXAMPLES

The density [g/$cm^3$] was determined in accordance with ISO 1183.

The determination of the molar mass distributions and the mean values $M_n$, $M_w$ and $M_w/M_n$ derived therefrom was carried out by means of high-temperature gel permeation chromatography using a method based on DIN 55672 under the following conditions: solvent: 1,2,4-trichlorobenzene, flow: 1 ml/min, temperature: 140° C., calibration using PE standards.

| | |
|---|---|
| cat. | catalyst |
| t(poly) | polymerization time |
| polymer | amount of polymer formed |
| $M_w$ | weight average molar mass |
| $M_n$ | number average molar mass |
| density | polymer density |
| prod. | productivity of the catalyst in g of polymer obtained per mmol of catalyst (chromium complex) used per hour. |

Example 1

1.1. Preparation of [2-(1H-inden-3-yl)methyl]pyridine

A mixture of 29.5 ml (0.3 mol) of alpha-picoline with 140 ml of tetrahydrofuran was cooled to −20° C. and 187.5 ml of n-butyllithium (1.6M in hexane, 0.3 mol) were subsequently added while stirring. The mixture was allowed to warm to room temperature while stirring and a solution of 39.6 g (0.3 mol) of 1-indanone in 35 ml of tetrahydrofuran was then added over a period of 25 minutes while stirring. The mixture was then stirred for a further 1.5 hours and hydrolyzed with 600 ml of dilute hydrochloric acid, the organic phase was separated off and the aqueous phase was extracted once with diethyl ether. The aqueous phase was then neutralized with aqueous ammonia solution and extracted 3 times with 150 ml each time of chloroform. The organic phases were combined and the solvent was distilled off. The 1-(2-pyridinylmethyl)-1-indanol obtained in this way was dissolved using 500 ml of 10% strength by weight hydrochloric acid and heated for 3 hours on a waterbath. The reaction mixture was cooled, washed with ether and the aqueous phase was neutralized with aqueous ammonia solution. The neutralized aqueous phase was extracted 3 times with 150 ml each time of chloroform and the combined organic phases were dried over magnesium sulfate. After the magnesium sulfate had been filtered off, the solvent was distilled off to leave 52.7 g of a mixture of 2-(1H-inden-3-ylmethyl)pyridine and 2-[(E)-2,3-dihydro-1H-inden-1-ylidenemethyl]pyridine in a ratio of 10:9 in a total yield of 95%. NMR $^1$H ($CDCl_3$): 8.61 (d, 1H); 7.61 (td, 1H); 7.55 (d, 1H); 7.51 (d, 1H); 7.36 (d, 1H); 7.32-7.22 (m, 3H); 7.16 (dd, 1H); 6.31 (m, 1H); 4.17 (br s, 2H); 3.43 (br s, 2H).

1.2. Preparation of (1-(2-pyridylmethyl)indenyl)chromium dichloride

A solution of 52.7 g of the above mixture of 2-(1H-inden-3-ylmethyl)pyridine and 2-[(E)-2,3-dihydro-1H-inden-1-ylidenemethyl]pyridine in a molar ratio of 10:9 in 550 ml of tetrahydrofuran was cooled to −100° C. 80.5 ml of a 15% strength n-butyllithium solution in hexane (0.1288 mol) were then slowly added dropwise. After the addition was complete, the reaction mixture was stirred at −100° C. for a further 45 minutes. The mixture was subsequently allowed to warm to room temperature. After stirring for a further 2 hours, the solution was cooled to 60° C. and 49 g (0.1288 mol) of chromium trichloride tris(tetrahydrofuran) were added while stirring. The mixture was allowed to warm slowly to room temperature and was subsequently stirred for a further 10 hours at room temperature. The reaction mixture was then refluxed for 20 minutes and subsequently cooled to room temperature. The solid which had precipitated was filtered off and washed with hot tetrahydrofuran. The solid was subsequently washed with diethyl ether and dried under reduced pressure. This gave 24.9 g of (1-(2-pyridylmethyl)indenyl)chromium dichloride (59%).

Example 2

2.1. Preparation of [2-1H-inden-3-yl)-1-methylethyl]pyridine

A solution of 7.25 g (0.046 mol) of 2-bromopyridine in 20 ml of diethyl ether was cooled to −60° C. and a mixture of 28.7 ml of n-butyllithium (1.6M in hexane, 0.046 mol) and 70 ml of diethyl ether was subsequently added while stirring. The mixture was stirred for a further 15 minutes and a solution of 7.16 g (0.046 mol) of 1-(1-methylethylidene)-1-indene dissolved in 10 ml of ether was then added. The mixture was allowed to warm to room temperature and was hydrolyzed with 100 ml of dilute hydrochloric acid. The organic phase was separated off, the aqueous phase was extracted once with diethyl ether, the aqueous phase was subsequently neutralized with aqueous ammonia solution and extracted three times with 50 ml each time of chloroform. The organic phases were combined, dried over magnesium sulfate, the magnesium sulfate was filtered off and the solvent was distilled off. This gave 0.54 g (5%) of [2-(1H-inden-3-yl)-1-methylethyl]pyridine.

2.2. Preparation of (3-(2-pyridyl-1-methylethyl)indenyl)chromium dichloride

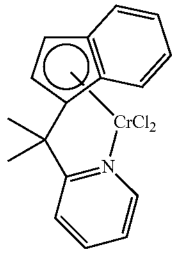

A solution of 0.54 g (0.0023 mol) of [2-(1H-inden-3-yl)-1-methylethyl]pyridine in 20 ml of tetrahydrofuran was cooled to −100° C. 1.72 ml of a 15% strength n-butyllithium solution in hexane (0.0027 mol) were slowly added dropwise. After the addition was complete, the reaction mixture was stirred at −100° C. for a further 30 minutes. The mixture was subsequently allowed to warm to room temperature. After stirring for a further 1 hour, the solution was cooled to −60° C. and 1.1 g (0.0029 mol) of chromium trichloride tris(tetrahydrofuran) were added while stirring. The mixture was allowed to warm slowly to room temperature and was subsequently stirred at room temperature for a further 10 hours. The reaction mixture was then refluxed for 20 minutes and subsequently cooled to room temperature. The solid which had precipitated was filtered off, washed with diethyl ether and dried under reduced pressure. This gave 0.3 g of (3-(2-pyridyl-1-methylethyl)indenyl)chromium dichloride (37%).

Example 3

3.1. Preparation of 2-isopropylpyridine

A solution of 19.4 ml (0.17 mol) of 2-ethylpyridine in 100 ml of tetrahydrofuran was cooled to −20° C. and 125 ml of n-butyllithium (1.6M in hexane, 0.2 mol) were subsequently added while stirring. The mixture was allowed to come to room temperature, stirred for another one hour and subsequently cooled back down to −20° C. A solution of 18 ml (0.25 mol) of methyl iodide in 20 ml of tetrahydrofuran was then added at such a rate that the temperature remained at −20° C. The mixture was allowed to warm to room temperature, stirred for a further 14 hours and hydrolyzed with 60 ml of water. The organic phase was separated off and the aqueous phase was extracted three times with 50 ml each time of diethyl ether. The organic phases were combined, dried over magnesium sulfate, the magnesium sulfate was filtered off and the solvent was distilled off. The residue obtained in this way was distilled at 81-84° C./60 torr. This gave 10.88 g (53%) of 2-isopropylpyridine.

3.2. Preparation of 2-[1-(1H-inden-3-yl)-1-methylethyl]pyridine

A solution of 10.8 g (0.09 mol) of 2-isopropylpyridine in 47 ml of tetrahydrofuran was cooled to −20° C. and 62.5 ml of n-butyllithium (1.6M in hexane, 0.11 mol) were subsequently added while stirring. The mixture was allowed to come to room temperature and was stirred for a further one hour. A solution of 15.84 g (0.12 mol) of 1-indanone in 12 ml of tetrahydrofuran was then added at such a rate that the temperature remained at 25° C. The mixture was stirred for a further 12 hours and hydrolyzed with 200 ml of dilute hydrochloric acid. The organic phase was separated off, the aqueous phase was extracted once with diethyl ether, the aqueous phase was subsequently neutralized with aqueous ammonia solution and was extracted three times with 100 ml each time of chloroform. The organic phases were combined, dried over magnesium sulfate, the magnesium sulfate was filtered off and the solvent was distilled off. This gave 16.6 g (77%) of 2-[1-(1H-inden-3-yl)-1-methylethyl]pyridine.

Example 4

4.1. Preparation of [2-(1H-inden-3-yl)(phenyl)methyl]pyridine

A mixture of 3.23 ml (0.02 mol) of 2-benzylpyridine in 15 ml of diethyl ether was cooled to −20° C. and 13 ml of n-butyllithium (1.6M in hexane, 0.02 mol) were subsequently added while stirring. The mixture was allowed to come to room temperature, stirred for another one hour and subsequently cooled to −60° C. A solution of 2.8 g (0.021 mol) of 1-indanone in 10 ml of diethyl ether was subsequently added while maintaining the temperature. The mixture was allowed to warm to room temperature, stirred for a further 3.5 hours and hydrolyzed with 40 ml of dilute hydrochloric acid. The solid which had precipitated was filtered off, the organic phase was separated off and the aqueous phase was extracted twice with ethyl acetate. The aqueous phase was then neutralized with aqueous ammonia solution and extracted three times with 30 ml each time of methylene chloride. The organic phases were combined, dried over magnesium sulfate, the magnesium sulfate was filtered off and the solvent was distilled off. Recrystallization of the residue obtained in this way from hexane gave 1.9 g (34%) of [2-(1H-inden-3-yl)(phenyl)methyl]pyridine.

4.2. Preparation of (3-(2-pyridyl-1-phenylmethyl)indenyl)chromium dichloride

A solution of 4.63 g (0.016 mol) of [2-(1H-inden-3-yl)(phenyl)methyl]pyridine in 60 ml of tetrahydrofuran was cooled to −100° C. 11 ml of a 15% strength n-butyllithium solution in hexane (0.016 mol) were slowly added dropwise. After the addition was complete, the reaction mixture was stirred at −100° C. for a further one hour. The mixture was subsequently allowed to warm to room temperature. After stirring for a further one hour, the solution was cooled to −60° C. and 6.15 g (0.016 mol) of chromium trichloride tris(tetrahydrofuran) was added while stirring. The mixture was allowed to warm slowly to room temperature and was subsequently stirred for another 10 hours at room temperature. The reaction mixture was then refluxed for 20 minutes and subsequently cooled to room temperature. The solid which had precipitated was filtered off, washed with diethyl ether and dried under reduced pressure. This gave 4.4 g of (3-(2-pyridyl-1-phenylmethyl)indenyl)chromium dichloride (40%).

Example 5

5.1. Preparation of 2-(1-methyl-4-pentenyl)pyridine

A solution of 8.46 ml (0.074 mol) of 2-ethylpyridine in 35 ml of tetrahydrofuran was cooled to −20° C. and 47 ml of n-butyllithium (15 w.-% in hexane, 0.074 mol) were subsequently added while stirring. The mixture was allowed to come to room temperature, stirred for another one hour and subsequently cooled back down to −20° C. A solution of 7.52 ml (0.074 mol) of 4-bromo-1-butene in 10 ml of tetrahydrofuran was then added at such a rate that the temperature remained at −20° C. The mixture was allowed to warm to room temperature, stirred for a further 14 hours and hydrolyzed with 50 ml of water. The organic phase was separated off and the aqueous phase was extracted three times with 30 ml each time of diethyl ether. The organic phases were combined, dried over magnesium sulfate, the magnesium sulfate was filtered off and the solvent was distilled off. The residue obtained in this way was distilled at 98-100° C./14 torr. This gave 8.95 g (75%) of 2-(1-methyl-4-pentenyl)pyridine.

5.2. Preparation of 2-[1-(1H-inden-3-yl)-1-methyl-4-pentenyl]pyridine

A solution of 8.95 g (0.0556 mol) of 2-(1-methyl4-pentenyl)pyridine in 50 ml of tetrahydrofuran was cooled to −20° C. and 35 ml of n-butyllithium (15 w.-% in hexane, 0.0556 mol) were subsequently added while stirring. The mixture was allowed to come to room temperature and was stirred for a further one hour. A solution of 7.33 g of 1-indanone in 8 ml of tetrahydrofuran was then added at such a rate that the temperature remained at 25° C. The mixture was stirred for a further 3 hours and hydrolyzed with 150 ml of dilute hydrochloric acid. The organic phase was separated off, the aqueous phase was extracted once with ethyl acetate, the aqueous phase was subsequently neutralized with aqueous ammonia solution and was extracted three times with 80 ml each time of dichloromethane. The organic phases were combined, dried over magnesium sulfate, the magnesium sulfate was filtered off and the solvent was distilled off. The crude product (about 10 g) was purified by column chromatography using a mixture of hexane:$CH_2Cl_2$=1:1 for the separation from starting 2-(1-methyl4-pentenyl)pyridine. Then, a mixture of hexane: $CH_2Cl_2$=1:2 was used. This gave 4.81 g (31%) of 2-[1-(1H-inden-3-yl)-1-methyl-4-pentenyl]pyridine.

5.3. Preparation of (3-(2-pyridyl-1-methyl-4-pentenyl)indenyl)chromium dichloride

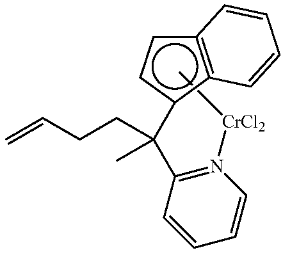

A solution of 4.81 g (0.01747 mol) of 2-[1-(1H-inden-3-yl)-1-methyl-4-pentenyl]pyridine in 60 ml of tetrahydrofuran was cooled to −100° C. 11.5 ml of a 15% strength n-butyllithium solution in hexane (0.01834 mol) were slowly added dropwise. After the addition was complete, the reaction mixture was stirred at −100° C. for a further 1 hour. The mixture was subsequently allowed to warm to room temperature. After stirring for a further 2 hour, the solution was cooled to −60° C. and 7.07 g (0.0189 mol) of chromium trichloride tris(tetrahydrofuran) were added while stirring. The mixture was allowed to warm slowly to room temperature and was subsequently stirred at room temperature for a further 10 hours. The solid which had precipitated was filtered off, washed with diethyl ether and dried under reduced pressure. Recrystallization from a mixture of dichloromethane and diethyle ether gave 2.5 g of (3-(2-pyridyl-1-methyl-4-pentenyl)indenyl)chromium dichloride (36%).

Comparative Example 1

5-[(2-Pyridyl)methyl]-1,2,3,4-tetramethylcyclopentadienylchromium dichloride was prepared by the method of WO 01/92346.

Polymerization

Polymerization was carried out at 40° C. under argon in a 1 l four-neck flask provided with contact thermometer, stirrer with Teflon blade, heating mantle and gas inlet tube. The appropriate amount of MAO (10% strength solution in toluene, Cr:Al=1:500) was added to a solution of the amount indicated in table 1 of the appropriate complex in 250 ml of toluene and the mixture was heated to 40° C. on a waterbath.

Shortly before introduction of ethylene, 3 ml of hexene were placed in the flask (only in the case of the copolymerizations) and ethylene was subsequently passed through the flask at a flow rate of about 20-40 l/h at atmospheric pressure. The remaining amount of hexene (as indicated in table 1 for the copolymerizations) was introduced via a dropping funnel over a period of 15 minutes. After the time indicated in table 1 under a constant ethylene flow, the polymerization was stopped by addition of methanolic HCl solution (15 ml of concentrated hydrochloric acid in 50 ml of methanol). 250 ml of methanol were subsequently added and the resulting white polymer was filtered off, washed with methanol and dried at 70° C.

TABLE 1

Polymerization results

| Catalyst from Ex. | Amount of cat. [mg] | t(poly) [min] | copolymerisation | amount of 1-hexene [ml] | Polymer [g] | Prod. [g/mmol Cr h] | $M_w$ [g/mol] | $M_w/M_n$ | Density [g/cm$^3$] |
|---|---|---|---|---|---|---|---|---|---|
| 4 | 9.6 | 12 | yes | 7 | 8.7 | 1836 | 238574 | 3.88 | 0.8898 |
| 5 | 9.8 | 10 | no | 0 | 6.1 | 1484 | 645785 | 6.26 | n.d. |

TABLE 1-continued

Polymerization results

| Catalyst from Ex. | Amount of cat. [mg] | t(poly) [min] | copoly-merisation | amount of 1-hexene [ml] | Polymer [g] | Prod. [g/mmol Cr h] | $M_w$ [g/mol] | $M_w/M_n$ | Density [g/cm$^3$] |
|---|---|---|---|---|---|---|---|---|---|
| 5 | 6.9 | 15 | yes | 6 | 5.6 | 1290 | 907820 | 3.82 | 0.9056 |
| C1 | 7.7 | 20 | yes | 7 | 12.8 | 1692 | 28067 | 4.61 | 0.94 |

Polymerization

The complex of example 1 was used in the polymerization of ethylene and in the copolymerization of ethylene and 1-hexene as described above for the complex of example 5 (using 3 and 9 ml hexene). The ethylene homopolymer obtained had a molecular weight Mw of 354078 g/mol. The ethylene-hexene copolymer however had a molecular weight Mw of only 283910 g/mol.

We claim:

1. A monocyclopentadienyl complex comprising formula $$(Cp)(\text{-}Z\text{-}A)_m MX_k \qquad \text{(VI)},$$

wherein

Cp is a cyclopentadienyl system of formula (II):

(II)

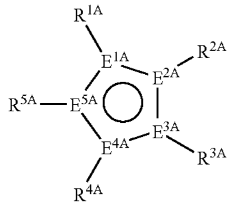

wherein:

$E^{1A}$-$E^{5A}$ are each carbon or phosphorus, with the proviso that not more than one of $E^{1A}$ to $E^{5A}$ is phosphorus;

$R^{1A}$-$R^{5A}$ are each, independently, hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, $SiR^{6A}_3$, or -Z-A, wherein $R^{1A}$-$R^{5A}$ are optionally substituted by at least one halogen, and two vicinal $R^{1A}$-$R^{5A}$ are optionally joined to form a five- or six-membered ring, with the proviso that one, two, or three of $R^{1A}$-$R^{5A}$ is -Z-A;

$R^{6A}$ are each, independently, hydrogen, a $C_1$-$C_{20}$-alkyl, a $C_2$-$C_{20}$-alkenyl, a $C_6$-$C_{20}$-aryl, or an alkylaryl comprising from 1 to 10 carbon atoms in the alkyl part and 6-20 carbon atoms in the aryl part, and two geminal $R^{6A}$ are optionally joined to form a five- or six-membered ring;

Z is —$CH(C_6H_5)$—

A comprises formula (III):

(III)

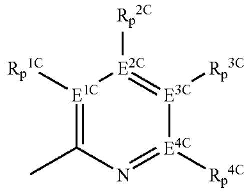

wherein $E^{1C}$-$E^{4C}$ are each carbon or nitrogen;

$R^{1C}$-$E^{4C}$ are each, independently, hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, or $SiR^{5C}_3$, wherein $R^{1C}$-$R^{4C}$ are optionally substituted by at least one halogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, or $SiR^{5C}_3$, and two vicinal $R^{1C}R^{4C}$, or $R^{1C}$ and Z are optionally joined to form a five- or six-membered ring;

$R^{5C}$ are each, independently, hydrogen, a $C_1$-$C_{20}$-alkyl, a $C_2$-$C_{20}$-alkenyl, a $C_6$-$C_{20}$-aryl or an alkylaryl comprising from 1 to 10 carbon atoms in the alkyl part and 6-20 carbon atoms in the aryl part, and two $R^{5C}$ are optionally joined to form a five- or six-membered ring;

p is 0 when $E^{1C}$-$E^{4C}$ is nitrogen, and 1 when $E^{1C}$-$E^{4C}$ is carbon;

M is a metal selected from the group consisting of titanium in an oxidation state 3, vanadium, chromium, molybdenum and tungsten;

m is 1, 2 or 3;

X are each, independently, fluorine, chlorine, bromine, iodine, hydrogen, a $C_1$-$C_{10}$-alkyl, a $C_2$-$C_{10}$-alkenyl, a $C_6$-$C_{20}$-aryl, an alkylaryl comprising 1-10 carbon atoms in the alkyl part and 6-20 carbon atoms in the aryl part, $NR^1R^2$, $OR^1$, $SR^1$, $SO_3R^1$, $OC(O)R^1$, CN, SCN, β-diketonate, CO, $BF_4^-$, $PF_6^-$, or a bulky noncoordinating anion;

$R^1$-$R^2$ are each, independently, hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, or $SiR^3_3$, wherein $R^1$-$R^2$ are optionally substituted by at least one halogen, and two $R^1$-$R^2$ are optionally joined to form a five- or six-membered ring;

$R^3$ are each, independently, hydrogen, a $C_1$-$C_{20}$-alkyl, a $C_2$-$C_{20}$-alkenyl, a $C_6$-$C_{20}$-aryl, or an alkylaryl comprising from 1 to 10 carbon atoms in the alkyl part and 6-20 carbon atoms in the aryl part, and two $R^3$ are optionally joined to form a five- or six-membered ring; and k is 1, 2, or 3.

2. A catalyst system for olefin polymerization comprising:

A) at least one monocyclopentadienyl complex of claim 1;

B) at least one activating compound;

C) optionally, an organic or inorganic support;

D) optionally, at least one catalyst suitable for olefin polymerization; and

E) optionally, at least one metal compound comprising a metal of group 1, 2 or 13 of the Periodic Table.

3. A process which comprises polymerizing at least one olefin in the presence of the catalyst system of claim 2.

* * * * *